(12) United States Patent
Zreda et al.

(10) Patent No.: US 11,249,036 B2
(45) Date of Patent: Feb. 15, 2022

(54) DISTANCE AND DIRECTION-SENSITIVE COSMOGENIC NEUTRON SENSORS

(71) Applicant: QUAESTA INSTRUMENTS, LLC, Tucson, AZ (US)

(72) Inventors: Marek Zreda, Tucson, AZ (US); Steven Hamann, Tucson, AZ (US); Martin Schrön, Leipzig (DE); Markus Köhli, Heidelberg (DE)

(73) Assignee: QUAESTA INSTRUMENTS, LLC, Tucson, AZ (US)

( * ) Notice: Subject to any disclaimer, the term of this patent is extended or adjusted under 35 U.S.C. 154(b) by 0 days.

(21) Appl. No.: 17/102,118

(22) Filed: Nov. 23, 2020

(65) Prior Publication Data

US 2021/0102906 A1 Apr. 8, 2021

Related U.S. Application Data

(63) Continuation-in-part of application No. 16/213,741, filed on Dec. 7, 2018, now Pat. No. 10,845,318.

(60) Provisional application No. 62/596,315, filed on Dec. 8, 2017.

(51) Int. Cl.
| | |
|---|---|
| *G01N 23/05* | (2006.01) |
| *G01N 23/09* | (2018.01) |
| *G01T 3/00* | (2006.01) |
| *G01N 23/02* | (2006.01) |

(52) U.S. Cl.
CPC .......... *G01N 23/09* (2013.01); *G01N 23/025* (2013.01); *G01T 3/008* (2013.01); *G01N 2223/616* (2013.01)

(58) Field of Classification Search
CPC .................. G01N 23/025; G01N 2223/616
See application file for complete search history.

(56) References Cited

U.S. PATENT DOCUMENTS

| | | |
|---|---|---|
| 2,928,965 A | 10/1954 | Bayard et al. |
| 4,047,042 A | 9/1977 | Wada et al. .................... 250/390 |
| 4,463,264 A | 7/1984 | Young et al. .................. 252/390 |
| 4,992,667 A | 2/1991 | Abelentsev et al. ...... 250/390.05 |
| 5,083,029 A | 1/1992 | Buchanan ................ 250/390.05 |
| 5,321,269 A | 6/1994 | Kitaguchi et al. ......... G01T 3/08 |
| 5,502,303 A | 3/1996 | Gonzalez-Lepera ...... 250/252.1 |

(Continued)

OTHER PUBLICATIONS

U.S. Appl. No. 16/213,741, filed Dec. 7, 2018.

(Continued)

*Primary Examiner* — David P Porta
*Assistant Examiner* — Shun Lee
(74) *Attorney, Agent, or Firm* — Hayes Soloway P.C.

(57) ABSTRACT

A local area cosmogenic neutron sensor is used for detecting moisture within a measurement surface. A neutron detector is positioned on a stand structure holding the detector above a measurement surface. A moderator material and neutron shield are positioned around at least a portion of the neutron detector. The neutron shield substantially covers lateral sides and an entirety of a top of the neutron detector and is not positioned on a bottom side of the neutron detector. A thermal neutron shield is positioned below the neutron detector and in a path of neutron travel between the measurement surface and the neutron detector to substantially block environmental thermal neutrons from reaching the neutron detector, which improves the signal-to-noise ratio and signal contrast of the local area cosmogenic neutron sensor.

20 Claims, 20 Drawing Sheets

(56) References Cited

U.S. PATENT DOCUMENTS

| | | | |
|---|---|---|---|
| 7,078,705 B1 | 7/2006 | Ianakiev et al. | 250/390.01 |
| 7,233,007 B2 | 6/2007 | Downing et al. | 250/390.11 |
| 7,514,694 B2 | 4/2009 | Stephan et al. | 250/390.01 |
| 8,217,360 B2 | 7/2012 | Nukatsuka et al. | 250/370.11 |
| 8,653,470 B2 | 2/2014 | Dubeau | 250/390.07 |
| 8,796,634 B2 | 8/2014 | Kisner et al. | G01T 3/008 |
| 9,029,788 B2 | 5/2015 | Yang et al. | G01T 3/06 |
| 9,081,100 B1 | 7/2015 | Bellinger et al. | G01T 3/08 |
| 9,329,303 B2 | 5/2016 | Inanc et al. | G01V 5/107 |
| 9,395,454 B2 | 7/2016 | Orava et al. | G01T 3/06 |
| 9,442,202 B2 | 9/2016 | Tanner et al. | G01T 3/00 |
| 9,678,229 B2 | 6/2017 | Neyland | G01T 3/008 |
| 9,778,392 B2 | 10/2017 | Justus et al. | |
| 9,817,138 B2 | 11/2017 | McGregor et al. | G01T 3/008 |
| 9,910,170 B1 | 3/2018 | Billiard et al. | G01T 3/02 |
| 9,939,538 B2 | 4/2018 | Ing et al. | G01T 3/065 |
| 9,958,561 B2 | 5/2018 | Bellinger et al. | G01T 3/065 |
| 9,978,384 B2 | 5/2018 | Li et al. | G01L 19/04 |
| 10,024,986 B2 | 7/2018 | Lennert et al. | G01T 3/008 |
| 10,564,112 B2 | 2/2020 | Zreda et al. | G01N 23/005 |
| 10,845,318 B2 | 11/2020 | Zreda et al. | G01N 23/005 |
| 2001/0046274 A1 | 11/2001 | Craig et al. | 376/154 |
| 2003/0012324 A1 | 1/2003 | Haruyama | 376/159 |
| 2004/0061047 A1 | 4/2004 | Bolozdynya et al. | 250/251 |
| 2006/0023828 A1 | 2/2006 | McGregor et al. | 376/158 |
| 2006/0138340 A1 | 6/2006 | Ianakiev et al. | 250/390.01 |
| 2008/0210880 A1 | 9/2008 | Baroni et al. | 250/390.11 |
| 2011/0180718 A1 | 7/2011 | Luszik-Bharda et al. | 250/390.03 |
| 2013/0341519 A1 | 12/2013 | Li et al. | G01T 3/06 |
| 2014/0158893 A1 | 6/2014 | Platt et al. | G01T 3/085 |
| 2014/0158895 A1 | 6/2014 | Wang et al. | G01T 3/008 |
| 2014/0361187 A1 | 12/2014 | Zhao et al. | G01T 3/06 |
| 2015/0014234 A1 | 1/2015 | Early et al. | B65D 90/10 |
| 2015/0241577 A1 | 8/2015 | Spillane et al. | G01T 3/00 |
| 2015/0355345 A1 | 12/2015 | Neyland | G01T 3/008 |
| 2016/0356901 A1 | 12/2016 | Shao et al. | G01T 3/08 |
| 2017/0023684 A1 | 1/2017 | Inglis et al. | G01T 3/008 |
| 2017/0059723 A1 | 3/2017 | Ing et al. | G01T 3/065 |
| 2017/0090049 A1 | 3/2017 | Ramsden et al. | G01T 3/06 |
| 2017/0184736 A1 | 6/2017 | Ramsden et al. | G01T 3/06 |
| 2017/0247737 A1 | 8/2017 | Gundry et al. | C12Q 1/06 |
| 2018/0299570 A1 | 10/2018 | Degtiarenko | G01T 7/00 |
| 2018/0341032 A1 | 11/2018 | Larue | G01T 3/00 |
| 2019/0178818 A1 | 6/2019 | Zreda et al. | G01N 23/00 |
| 2020/0036325 A1 | 1/2020 | Poivet | H02S 30/10 |

OTHER PUBLICATIONS

Desilets, D., and M. Zreda, 2013. Footprint diameter for a cosmic-ray soil moisture probe: Theory and Monte Carlo simulations. Water Resources Research 49, 3566-3575, doi: 10.1002/wrcr.20187 (10 pgs).

Fragopoulou et al. Shielding around spallation neutron sources, Journal of Physics: Conference Series vol. 41, pp. 514-581 (Year: 2006).

Heidbüchel et al., "Use of cosmic-ray neutron sensors for soil moisture monitoring in forests" *Hydrol. Earth Syst. Sci.*, 20, 1269-1288, 2016.

"Insights into the footprint of the cosmic-ray probe from new field measurements and neutron modeling," COSMOS 5 Workshop, Copenhagen, Aug. 22-24, 2016 (63 pgs).

Knoll, G.F., 2000, Radiation detection and measurement: New York, Wiley, 802 p. (82 pgs), relevant pp. 55-57, 159-173 and 505-520.

Köhli, M., M. Schrön, M. Zreda, U. Schmidt, P. Dietrich, and S. Zacharias, 2015. Footprint characteristics revised for field-scale soil moisture monitoring with cosmic-ray neutrons. Water Resources Reseach 51, 5772-5790 (20 pgs).

Lab C Website, www.lab.c.co (7 pgs), dated Dec. 18, 2018.

Schrön, M., M. Köhli, L. Scheiffele, J. Iwema, H.R. Bogena, L. Lv, E. Martini, G. Baroni, R. Roselem, J. Weimar, J. Mai, M. Cuntz, C. Rebmann, S.E. Oswald, P. Dietrich, U. Schmidt, and S. Zacharias, 2017b. Improving calibration and validation of cosmic-ray neutron sensors in the light of spatial sensitivity. Hydrology and Earth System Sciences 21, 5009-5030 (22 pgs). Published Oct. 6, 2017.

Schrön, M., Zacharias, S., Womack, G., Köhli, M., Desilets, D., Oswald, S. E., Bumberger, J., Mollenhauer, H., Kögler, S., Remmler, P., Kasner, M., Denk, A., and Dietrich, P., 2017a. Intercomparison of Cosmic-Ray Neutron Sensors and Water Balance Monitoring in an Urban Environment, Geoscientific Instruments, Methods and Data Systems Discussions, https://doi.org/10.5194/gi-2017-34, in review (18 pgs). Published Mar. 9, 2018.

Zreda, M., D. Desilets, T.P.A. Ferré, and R.L. Scott, 2008. Measuring soil moisture content non-invasively at intermediate spatial scale using cosmic-ray neutrons. Geophysical Research Letters 35, L21402, doi:10.1029/2008GL035655 (5 pgs).

Zreda, M., W.J. Shuttleworth, X. Zeng, C. Zweck, D. Desilets, T. Franz, and R. Rosolem, 2012. COSMOS: the COsmic-ray Soil Moisture Observing System. Hydrology and Earth System Sciences 16, 4079-4099 (23 pgs).

International Preliminary Report on Patentability issued in PCT/US18/64548 dated Jun. 9, 2020 (8 pgs).

International Preliminary Report on Patentability issued in PCT/US18/64573 dated Jun. 9, 2020 (6 pgs).

International Search Report and Written Opinion issued in PCT/US2018/064548 dated Feb. 19, 2019, 11 pgs.

International Search Report and Written Opinion issued in PCT/US2018/064573 dated Feb. 14, 2019, 9 pgs.

Office Action issued in U.S. Appl. No. 16/213,812 dated Feb. 15, 2019, 20 pgs.

Office Action issued in U.S. Appl. No. 16/213,812 dated Aug. 16, 2019, (16 pgs).

Office Action issued in U.S. Appl. No. 16/213,741 dated Feb. 8, 2019, 9 pgs.

Office Action issued in U.S. Appl. No. 16/213,741 dated Mar. 7, 2019, 18 pgs.

Office Action issued in U.S. Appl. No. 16/213,741 dated Jul. 9, 2019, 22 pgs.

Office Action issued in U.S. Appl. No. 16/213,741 dated Jan. 14, 2020, 18 pgs.

Office Action issued in U.S. Appl. No. 16/213,741 dated Mar. 3, 2020, 11 pgs.

Notice of Allowance issued in U.S. Appl. No. 16/213,812, dated Oct. 8, 2019, 6 pages.

Notice of Allowance issued in U.S. Appl. No. 16/213,741, dated Jul. 20, 2020. 9 pages.

Andreasen et al., "Cosmic-ray neutron transport at a forest field site: the sensitivity to various environmental conditions with focus on biomass and canopy interception", Hydrology and Earth System Sciences, vol. 21, No. 4, Apr. 3, 2017, 20 pgs.

Dhairyawan et al., "Response Functions of Spherically Moderated Neutron Detectors", Nuclear Instruments and Methods, vol. 169, No. 1, Feb. 1980, pp. 115-120.

Desilets et al., "Nature's neutron probe: Land surface hydrology at an elusive scale with cosmic rays", Water Resources Research, vol. 46, No. 11, Nov. 1, 2010, 7 pgs.

Rees, et al., "Optimizing moderation of He-3 neutron detectors for shielded fission sources", Nuclear Instruments and Methods in Physics Research, vol. 691, Jul. 2012, pp. 72-80.

Schrön et al., "Monitoring Environmental Water with Ground Albedo Neutrons and Correction for Incoming Cosmic Rays with Neutron Monitor Data", Proceedings of Science, 34 [th] International Cosmic Ray Conference, Jul. 30-Aug. 6, 2015, accessed by EP Examiner on Sep. 2, 2021 at: https://inspirehep.net/files/3062ae9e5el9a266535c5147bc2f3b5f, 8 pgs.

Zreda et al., "Cosmic-ray neutron probe: non-invasive measurement of soil water content", Dept. of Hydrology and Water Resources, Univ. of Arizona, undated, accessed by EP Examiner on Sep. 2, 2021 at: http://quebec.hwr.arizona.edu/research/agu05-zfeda-cosmic-ray-neutron-probe.pdf, 1 pg.

Zreda et al., "COSMOS: the COsmic-ray Soil Moisture Observing System", Hydrology and Earth System Sciences, vol. 16, Nov. 7, 2012, 21 pgs.

(56) References Cited

OTHER PUBLICATIONS

Yamashita, et al., "Detection Efficiency of Bare and Moderated BF3-Gas-Filled Proportional Counters for Isotropic Neutron Fluxes", Journal of Nuclear Science and Technology, vol. 3, No. 8, Aug. 1966, pp. 343-353.
European Search Report issued in EP Application No. 18 885 680.1, dated Jul. 20, 2021, 14 pgs.
European Search Report issued in EP Application No. 18 887 019.0, dated Sep. 2, 2021, 13 pgs.
International Search Report and Written Opinion issued in PCT/US21/54591 dated Nov. 30, 2021, 9 pgs.

Method Of Calibrating A Local Area Cosmogenic Neutron Sensor For Soil Moisture Detection Provide a hydrogen-sensitive neutron detector and a neutron shield positioned to interact with cosmogenic neutrons propagating from a wide area of a measurement surface below the hydrogen-sensitive neutron detector
1710

↓

Orient the hydrogen-sensitive neutron detector above a first measurement surface
1720

↓

Measure the neutron intensity of the first measurement surface
1730

↓

Calibrate a cosmogenic neutron sensor based on the measured neutron intensity of the first measurement surface and at least one additional data point
1740

FIG. 17A

Method Of Wide Area Calibration Of A Wide Area Cosmogenic Neutron Sensor For Soil Moisture Detection Determine at least two local area calibration functions, each determined by: providing a hydrogen-sensitive neutron detector and a neutron shield positioned to interact with cosmogenic neutrons propagating from a wide area of a measurement surface below the hydrogen-sensitive neutron detector; orienting the hydrogen-sensitive neutron detector above a first measurement surface; measuring the neutron intensity of the first measurement surface; and calibrating a cosmogenic neutron sensor based on a defined measured neutron intensity of the first measurement surface and at least one additional data point to produce a local area calibration function
1750

Calibrate a wide area cosmogenic neutron sensor based on the at least two determined local area calibration functions and a weighting function.
1760

FIG. 17B

DISTANCE AND DIRECTION-SENSITIVE COSMOGENIC NEUTRON SENSORS

CROSS REFERENCE TO RELATED APPLICATION

This application is a continuation-in-part application of U.S. patent application Ser. No. 16/213,741 entitled, "Distance and Direction-Sensitive Cosmogenic Neutron Sensors" filed Dec. 7, 2018, which itself claims benefit of U.S. Provisional Application Ser. No. 62/596,315, titled "Distance and Direction Sensitive Cosmogenic-Neutron Soil Moisture Sensors (CNS)," filed Dec. 8, 2017, the entire disclosures of which is incorporated herein by reference.

FIELD OF THE DISCLOSURE

The present disclosure is generally related to measuring the moisture content of materials and more particularly is related to measuring moisture by non-invasively measuring the density of cosmogenic neutrons at and above the surface of materials.

BACKGROUND OF THE DISCLOSURE

Measuring the moisture content of materials such as surface soils using cosmogenic neutron detection is known in the art. Cosmic rays continually bombard the Earth and penetrate into materials at the land surface, including soil, atmosphere, water, man-made structures, vegetation, and the like. Inside these materials, cosmogenic high-energy (>10 MeV) neutrons collide with matter and produce fast (<2 MeV) cosmogenic neutrons. These neutrons interact with matter in reactions called neutron scattering that lead to the gradual decrease of neutron energies and eventually to the removal of neutrons from the environment. Hydrogen is by far the most efficient element in scattering neutrons. Therefore, moisture content of the soil through which neutrons have traveled can be inferred from the measured neutron flux, which is inversely correlated with soil moisture content. This principle has been used to develop a cosmogenic neutron soil moisture measuring method widely accepted around the world.

However, there are limitations to this method. At any given location near the land surface, neutrons are present that have interacted with the land surface material anywhere from the near field (within meters of the location) to the far field (or wide-area, hundreds of meters from the location). This reduces the accuracy of measurements by introducing a disproportionate amount of signal to the detector, as the local intensity of cosmogenic neutrons may not reflect average water content of the material over this broad region.

Additionally, neutron detectors must be calibrated. Calibration of cosmogenic neutron probes is typically done by comparing neutron measurements with independently obtained soil moisture to obtain calibration parameter $N_0$ (neutron intensity that would be measured above a completely dry soil). Independent soil moisture is obtained by collecting a large number (typically 108, prescribed by Zreda et al., 2012) of soil samples within the hectometer-sized footprint and measuring soil water content by the gravimetric (oven drying) method. This is a difficult, time-consuming and expensive process. Additionally, it does not work in soils with stones, as sample collection is difficult, in areas with rock outcrops, and in areas with organic litter covering soil.

Thus, a heretofore unaddressed need exists in the industry to address the aforementioned deficiencies and inadequacies.

SUMMARY OF THE DISCLOSURE

Embodiments of the present disclosure provide a local area cosmogenic neutron sensor for detecting moisture within a measurement surface. Briefly described, in architecture, one embodiment of the sensor, among others, can be implemented as follows. A neutron detector is positionable above the measurement surface, wherein a moderator material is positioned around at least a portion of the neutron detector to form a moderated neutron detector. A neutron shield is positioned around a portion of the moderated neutron detector, whereby the neutron shield substantially covers lateral sides of the moderated neutron detector and substantially an entirety of a top of the moderated neutron detector, wherein the neutron shield is positioned to interact with cosmogenic neutrons propagating to the lateral sides or the top of the moderated neutron detector, thereby substantially blocking fast, epithermal, and thermal cosmogenic neutrons propagating to the lateral sides or the top of the moderated neutron detector from reaching the moderated neutron detector, and wherein the neutron shield is not positioned on a bottom side of the moderated neutron detector. A thermal neutron shield is positioned below the neutron detector. A stand structure holds the moderated neutron detector and the neutron shield in a position a spaced vertical distance above the measurement surface with the bottom side of the moderated neutron detector facing the measurement surface. Local area cosmogenic neutrons propagating from the measurement surface below and near the moderated neutron detector travel through an air space before arriving at the thermal neutron shield, wherein environmental thermal neutrons are blocked from arriving at bottom side of the moderated neutron detector.

The present disclosure can also be viewed as providing a local area cosmogenic neutron sensor for detecting moisture within a measurement surface and having an improved signal-to-noise ratio and signal contrast. Briefly described, in architecture, one embodiment of the sensor, among others, can be implemented as follows. A neutron detector is positioned on a stand structure. The stand structure holds the neutron detector a spaced vertical distance above a measurement surface. A moderator material is positioned around at least a portion of the neutron detector. A neutron shield is positioned around a portion of the neutron detector and moderator material, whereby the neutron shield substantially covers lateral sides of the neutron detector and substantially an entirety of a top of the neutron detector, wherein the neutron shield is positioned to interact with cosmogenic neutrons propagating to the lateral sides or the top of the neutron detector, thereby substantially blocking cosmogenic neutrons propagating to the lateral sides or the top of the neutron detector from reaching the neutron detector, and wherein the neutron shield is not positioned on a bottom side of the neutron detector. A thermal neutron shield is positioned below the neutron detector and in a path of neutron travel between the measurement surface and the neutron detector, wherein the thermal neutron shield substantially blocks environmental thermal neutrons from reaching the neutron detector.

The present disclosure can also be viewed as providing a method for detecting local area cosmogenic neutrons for use in detecting moisture within a measurement surface. In this regard, one embodiment of such a method, among others, can be broadly summarized by the following steps: positioning a neutron detector above the measurement surface, wherein a moderator material is positioned around at least a portion of the neutron detector to form a moderated neutron detector; placing a neutron shield around a portion of the moderated neutron detector, whereby the neutron shield substantially covers lateral sides of the moderated neutron detector and substantially an entirety of a top of the moderated neutron detector, whereby the neutron shield is positioned to interact with cosmogenic neutrons propagating to the lateral sides or the top of the moderated neutron detector, thereby substantially blocking fast, epithermal, and thermal cosmogenic neutrons propagating to the lateral sides or the top of the moderated neutron detector from reaching the moderated neutron detector, and wherein the neutron shield is not positioned on a bottom side of the moderated neutron detector; placing a thermal neutron shield in a position below the neutron detector; and spacing the moderated neutron detector a spaced vertical distance about the measurement surface with a stand structure, whereby the bottom side of the moderated neutron detector faces the measurement surface, whereby local area cosmogenic neutrons propagating from the measurement surface below and near the moderated neutron detector travel through an air space before arriving at the thermal neutron shield, whereby environmental thermal neutrons are blocked from arriving at bottom side of the moderated neutron detector.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 17A is a flow chart showing a method of calibrating a local area cosmogenic neutron detector for soil moisture detection, in accordance with a second exemplary embodiment of the present disclosure.

FIG. 17B is a flow chart showing a method of wide area calibration of a cosmogenic neutron detector for soil moisture detection, in accordance with the second exemplary embodiment of the present disclosure.

DETAILED DESCRIPTION

Detectors that can be used for measuring the intensity of cosmogenic neutrons near the land surface have been known for decades (Knoll, 2000), and dedicated sensors for measuring soil moisture have been around for approximately ten years (Zreda et al., 2008, 2012). Such sensors, which we call Cosmogenic Neutron Sensors (CNS), measure the local intensity of neutrons in an energy band that is dictated by the design of the sensor. An unmoderated, or bare, thermal neutron detector is sensitive to thermal neutrons having a median energy of 0.025 eV. Adding a plastic moderator around the thermal neutron detector shifts the energy sensitivity of the thermal neutron detector to neutrons having higher energies. An energy band may be selected to optimize the ability of the sensor to detect neutrons that have maximum sensitivity to water in the material near the surface. The standard CNS (Zreda et al., 2012) has 2.5 cm of plastic surrounding the bare detector. It measures neutrons in energy band 1 eV to 1000 eV, which is sensitive to hydrogen content.

The intensity of cosmogenic fast neutrons displays a complex spatial pattern around the neutron measuring device, with contributions that vary with direction and distance. The current neutron sensors count neutrons coming from all directions and distances and produce a single integral value of neutron intensity; the directional and distance information is lost in the integration process. That measured value is converted to an integrated value of soil moisture by means of a calibration function.

The distance that contributes 86.5% (1-e-2) of neutrons counted is considered the effective measurement range of a cosmogenic sensor, or its "footprint". The physical spatial neutron distribution that reflects the probability of a measured neutron originating from the material at a given distance is called the spatial sensitivity function of the neutrons. In the very common case of radial symmetry, the function is referred to as the radial sensitivity function. When the cosmogenic method for measuring soil moisture was developed, its developers determined from neutron transport modeling that the radial sensitivity function follows exponential decay with distance (Desilets and Zreda, 2013; "conventional" in FIG. 1). But recent modeling results (Köhli et al., 2015; Schrön et al., 2017b), as well as our own field measurements, suggest a different radial sensitivity that can be approximated by double-exponential functions.

Figure 1B:
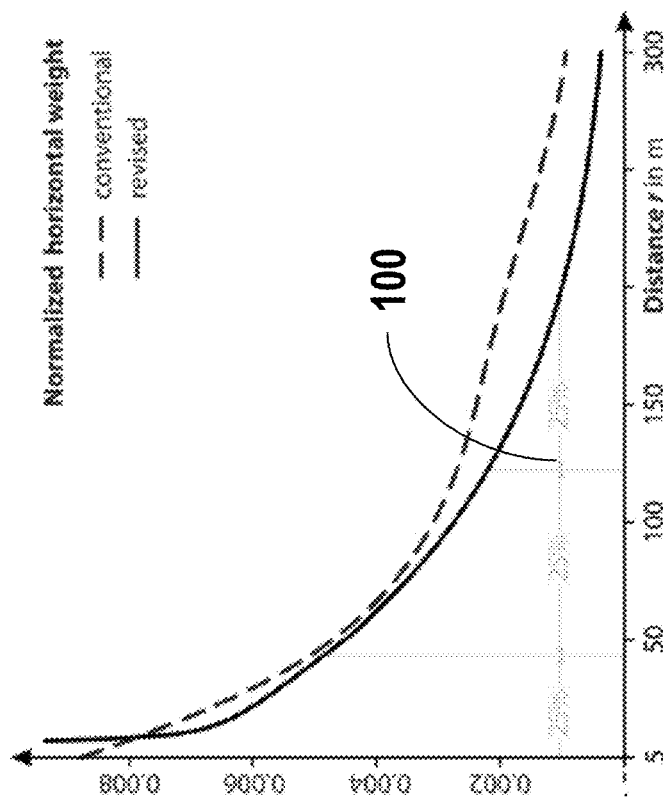
FIGS. 1A-1B are graphs showing the radial sensitivity functions for conventional and revised models of cosmogenic soil moisture probes.
Figure 1A:
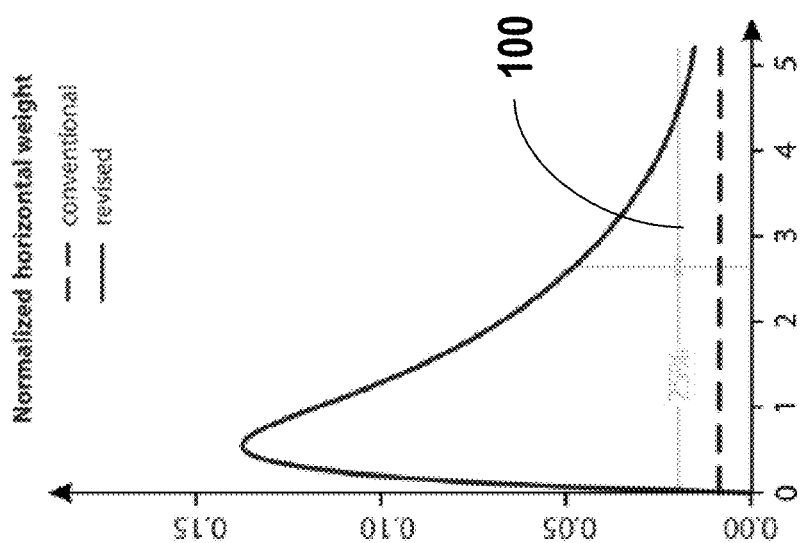

FIGS. 1A-1B are graphs showing the radial sensitivity functions for conventional and revised models of cosmogenic soil moisture probes. The normalized horizontal weight for the conventional model is shown in broken lines, while the normalized horizontal weight for the revised model is shown in solid lines. The boundaries of fractional contribution 100 are indicated below the curves in both FIGS. 1A and 1B. The conventional radial sensitivity function of Desilets and Zreda (2013) is an exponential curve, and the revised radial sensitivity function of Schrön et al. (2017b) is a double exponential curve. FIG. 1B shows that both conventional and revised models are similar at radial distances greater than 10 meters. FIG. 1A shows that the models are very different at shorter distances from 0 meters to about 5 meters.

In FIG. 1A, the boundaries of fractional contribution 100 indicate that, up to a distance just under 3 meters, the neutron contribution to the total measurement of a CNS is about 25%. Thus, the neutrons that come from short distances contribute a large fraction of the total measured neutron intensity, thereby interfering with wide-area measurement. In FIG. 1B, the boundaries of fractional contribution 100 indicate that another 25% of the neutrons in the total measurement come from distances less than 50 meters, while another 25% comes from distances between that point and about 120 meters.

Critically, the contribution to the total neutron count is not uniform within the footprint, with a large proportion coming from the first few meters around a detector. This important fact was not well understood among the community of CNS experts. The ability separately to measure local and wide-area neutrons would represent a powerful improvement to the CNS technique. However, such measurement discrimination is impossible with the currently-used cosmogenic soil moisture measuring devices, as they are not capable of discerning which neutrons have contributed to the total measurement.

Figure 2:
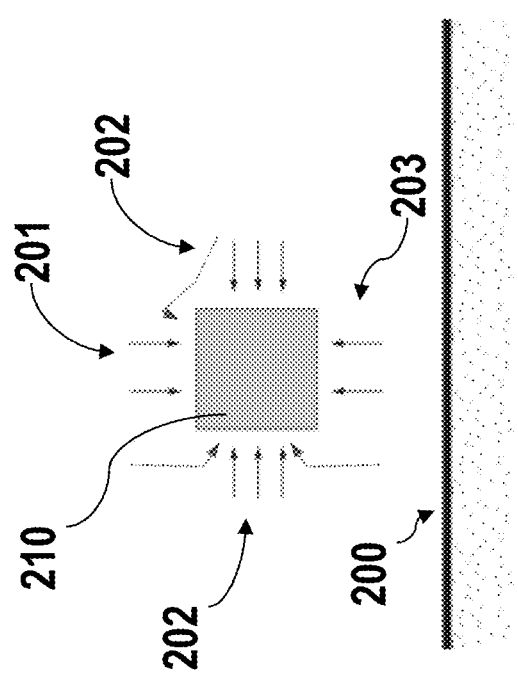
FIG. 2 is an illustration of the neutron sources incident upon a neutron detector.

FIG. 2 is an illustration of the neutron sources incident upon a neutron detector 210. A neutron detector 210 is shown oriented above a measurement surface 200. In use, the measurement surface 200 may be the ground, construction, a body of water, and the like. Neutrons are incident upon the detector 210 from overhead, from the wide area below the detector 210, and from the local area below the detector 210.

The measured neutron intensity contains neutrons coming directly from above the detector 210, also called overhead neutrons 201. These overhead neutrons 201, when corrected for the effects of solar activity, atmospheric pressure, latitude and longitude, and other conditions, constitute a constant background in all measurements. They have no history of interactions with soil water, and are therefore generally undesirable. Removal of overhead neutrons 201 may decrease the noise, and thus improve the sensitivity and accuracy of the neutron sensor 210 to changes in soil moisture. This in turn improves the signal-to-noise ratio and increases the dynamic range of the CNS method.

The measured neutron intensity also contains a significant amount of neutrons coming from areas below the detector 210 that are several meters or hectometers away from the detector 210, also called wide area neutrons 202. Although the area enclosed within less than 10 m radius around the detector contributes approximately one-third to the total number of neutrons measured, a significant remainder of the detected neutrons are wide area neutrons.

The measured neutron intensity also contains a significant amount of neutrons coming from areas below the detector 210 that are near the detector 210, also called local area neutrons 203. The neutrons coming from below the detector 210 can distort the measurement of wide area average moisture value.

This is important for at least two reasons. First, an accurate measurement of a wide area measurement surface should minimize the local area neutrons 203. If wide-area measurement is desired, the neutrons coming from below should be reduced or substantially eliminated. Second, an accurate measurement of a local area measurement surface should minimize the wide area neutrons 202. High sensitivity to local area neutrons 203 can be used to measure near-field (within meters) soil moisture. However, because far-field neutrons (those beyond a few meters from the detector 210) contribute approximately 70% to the total neutrons measured, they have to be blocked if near-field measurement is desired.

Furthermore, the neutrons coming from below and above the detector 201, 203 make up approximately 50% of the measured total neutrons, although this number depends on soil moisture and other local conditions. The remaining ~50% are wide area neutrons 202 coming from the sides from distances between a few meters and a few hectometers. These numbers represent average distributions of neutrons coming from above, below, and to the side of the detector 210. There may be some directional overlapping of neutrons from any direction. For example, a portion of neutrons 201 may not hit the detector 210 from above, but may enter from the side. A portion of neutrons 202 may hit the detector 210 from above rather than from the side. This representation of neutrons 201, 202, and 203 and their directions with respect to the detector 210 merely indicates that neutrons are probabilistically likely to come from these respective directions. Given these distributions, the ability preferentially to select these neutrons is desirable, even required, for proper wide-area measurement of soil moisture.

Figure 3A:
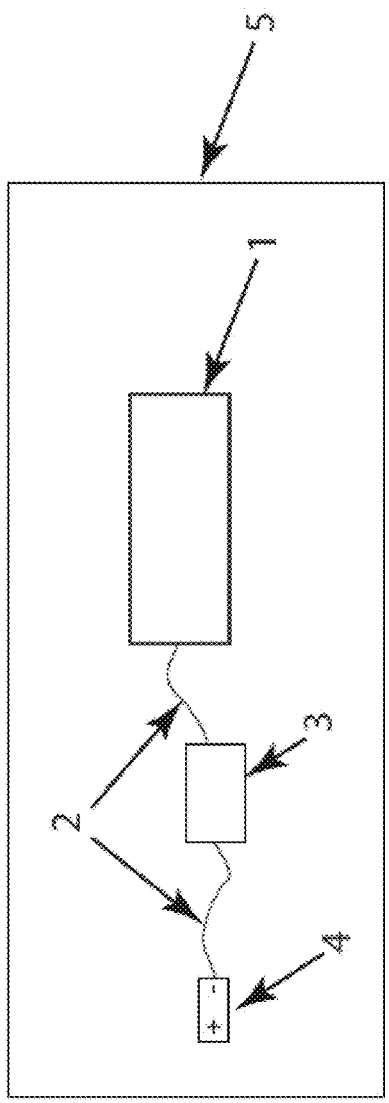
FIGS. 3A-3B are illustrations of the prior art moderated cosmogenic neutron sensors.
Figure 3B:
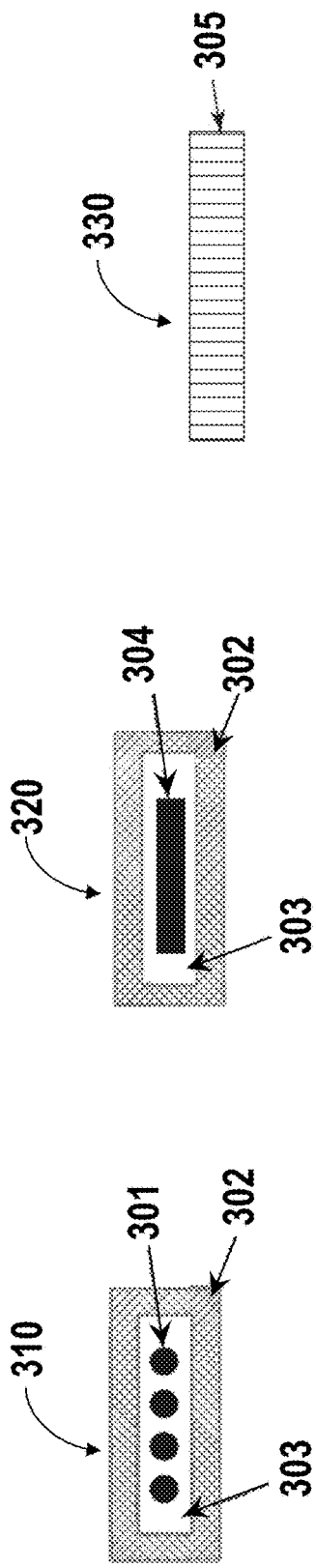

FIG. 3A is an illustration of the prior art cosmogenic neutron sensor 5. The moderated cosmogenic neutron sensor 5 of the prior art may include a hydrogen-sensitive neutron detector 1. The hydrogen-sensitive neutron detector 1 may include a thermal neutron detector surrounded by a neutron moderator, as shown in FIG. 3B. The neutron moderator may be made from a moderating material, such as polyethylene, that makes the thermal neutron detector sensitive to epithermal neutrons in a desired energy range. The signal from hydrogen-sensitive neutron detector 1 may be transmitted via a cable 2 to electronic modules and data logger 3. A power supply 4 may provide power to the hydrogen-sensitive neutron detector 1. As shown in FIG. 2, above, the prior art cosmogenic neutron sensor 5 may receive neutrons from overhead, from a wide area, and from a local area.

FIG. 3B is an illustration of exemplary prior art hydrogen-sensitive neutron detectors 310, 320, 330. Hydrogen-sensitive neutron detector 310 includes a thermal neutron detector 301, which is a gas proportional counter. Thermal neutron detector 301 may include a moderator 302 surrounding the thermal neutron detector 301, with a space 303 in between. The space 303 may generally be a vacuum or an air-filled space. Hydrogen-sensitive neutron detector 320 includes a thermal neutron detector 304, which is a lithium foil detector. Thermal neutron detector 304 may include a moderator 302 surrounding the thermal neutron detector 304, with a space 303 in between. Hydrogen-sensitive neutron detector 330 includes a fast neutron detector 305, which may be a scintillator detector. Other hydrogen-sensitive neutron detectors may be included the scope of this disclosure.

It should be noted that, in the drawings, areas shown with parallel line hatching indicate neutron shields. Areas shown with cross hatching indicate moderators. And areas shown with stippling indicate constant hydrogen materials.

Figure 4:
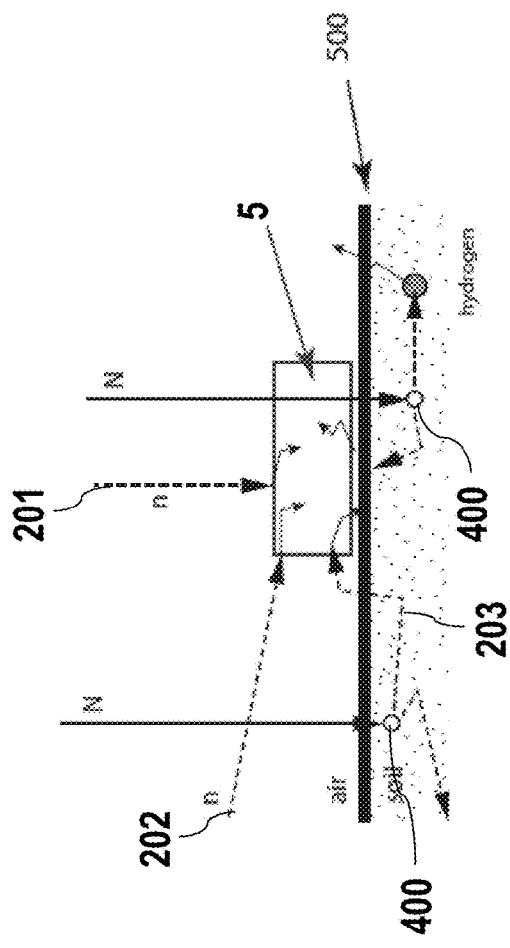
FIG. 4 is an illustration of neutrons impinging upon the prior art moderated cosmogenic neutron sensor.

FIG. 4 is an illustration of neutrons 201, 202, 203 impinging upon the prior art moderated cosmogenic neutron sensor 5. Cosmogenic neutrons 400 propagate from space to objects and soil on earth. The cosmogenic neutrons 400 may become overhead neutrons 201, which impinge upon the moderated cosmogenic neutron sensor 5 without interacting with any objects or soil. The cosmogenic neutrons 400 may interact with objects or hydrogen in soil and become wide area or local area neutrons 202, 203. Wide and local area neutrons 202, 203, along with overhead neutrons 201, may propagate toward and impinge upon the moderated cosmogenic neutron sensor 5, reaching the thermal neutron sensor 5 and causing a measurement to be made from all directions of the neutron sources. The moderated cosmogenic neutron sensor 5 may detect the total intensity of all neutrons impinging upon the cosmogenic neutron sensor 5.

Figure 5A:
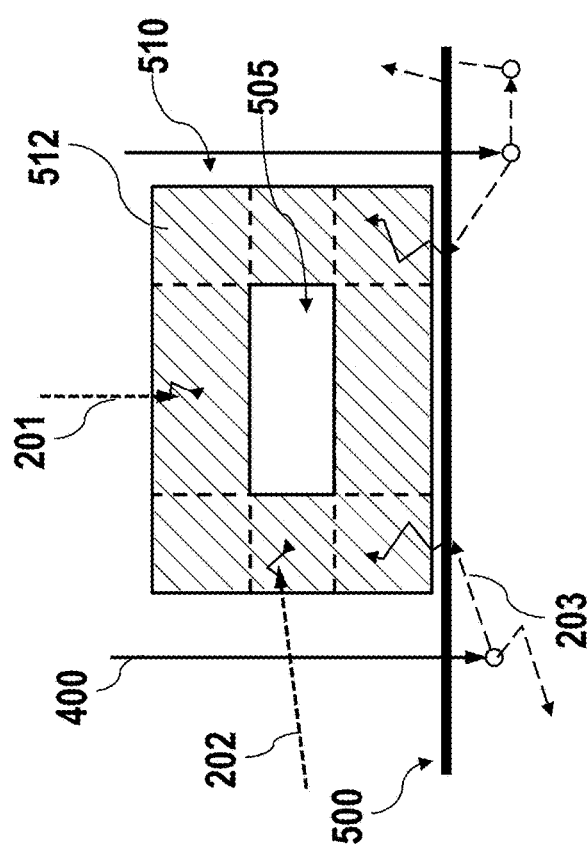
FIGS. 5A-5E are illustrations of cosmogenic neutron sensors in accordance with a first exemplary embodiment of the present disclosure.

FIG. 5A is an illustration of a cosmogenic neutron detector 510 in accordance with a first exemplary embodiment of the present disclosure. The cosmogenic neutron detector 510 includes a hydrogen-sensitive neutron detector 505 orientable above a measurement surface 500. A neutron shield 512 is positionable on the hydrogen-sensitive neutron detector 505. The neutron shield 512 is positioned to interact with at least a portion of cosmogenic neutrons 201, 202, 203 propagating in a direction of the hydrogen-sensitive neutron detector 505.

The hydrogen-sensitive neutron detector 505 may be any suitable type of neutron detector, including gas-proportional detectors with moderator, scintillation neutron detectors, semiconductor neutron detectors, and others. The hydrogen-sensitive neutron detector 505 may respond to energies between 0 and 2 MeV, or any subrange thereof. The hydrogen-sensitive neutron detector 505 may be sized and shaped to detect cosmogenic neutrons over a desired area or with a desired sensitivity. The hydrogen-sensitive neutron detector 505 may include a moderator to make the hydrogen-sensitive neutron detector 505 sensitive to a desired range of neutrons. The hydrogen-sensitive neutron detector 505 may detect neutrons from all directions without discrimination.

The term "neutron detector" 505 in this disclosure may refer to any suitable type of hydrogen-sensitive neutron detector, with or without a moderator, as some neutron sensors do not require moderated neutrons. For ease of representation in the drawings, the neutron detector 505 may generally be shown as a box. However, the box is a diagrammatic representation only; the neutron detector 505 may actually include one or more tube detectors, sheet detectors, or moderators.

The neutron detector 505 is orientable above a measurement surface 500. The neutron detector 505 may be oriented in any suitable direction, whether vertically or horizontally, depending on the desired use. The measurement surface 500 may be an area or surface below the cosmogenic neutron sensor 510 of any size, elevation, and material. In one example, the measurement surface 500 may be an area of land having dirt, soil, rocks, water, urban construction, or some combination thereof. The measurement surface 500 may have a local area, a wide area, and an intermediate area. The local area may be a portion of the measurement surface 500 located immediately below the physical footprint of the neutron detector 505, and often, the radial location below and within several meters of the cosmogenic neutron sensor 510. In one example, the local area may be located within 1, meter, 2, meters, 3, meters, 5, meters, or greater of the cosmogenic neutron sensor 510. The wide area may be a portion of the measurement surface 500 located further away from the cosmogenic neutron sensor 510. In one example, the wide area may begin where the local area ends, and may continue to the extent of the measurement surface. For instance, if, hypothetically, the local area is located within about 5 meters of the cosmogenic neutron sensor 510, the wide area may begin at about 5 meters from the cosmogenic neutron sensor 510 and may continue until the end of the measurement area. The intermediate area may be a portion of the measurement surface 500 located between the local area and the wide area. For example, the intermediate area may include a portion of the local area and a portion of the wide area.

The neutron detector 505 may be oriented above the measurement surface 500 in use. Where the measurement surface 500 is generally land or water, this means that the neutron detector 505 may be positioned vertically or horizontally above the measurement surface 500. This may cause overhead neutrons 201 to propagate toward the cosmogenic neutron sensor 510 substantially from above, while local area and wide area neutrons 203, 202 propagate toward the cosmogenic neutron sensor 510 substantially from below and from the sides, respectively.

The neutron shield 512 may be positionable on the neutron detector 505. The shield 512 interacts with neutrons 201, 202, 203 propagating in a direction of the neutron detector 505 by causing them to be substantially blocked. This may prevent the neutrons 201, 202, 203 from reaching the neutron detector 505. For the purposes of this disclosure, "interact" means to prevent a neutron from reaching the neutron detector 505 in the measurable energy range. Therefore, when the shield 512 interacts with the neutrons 201, 202, 203 propagating in a direction of the neutron detector 505, the shield 512 causes those neutrons to either fail to reach the neutron detector 505, or to fail to reach the neutron detector 505 with a measurable strength, which, in the field of neutron detector, is equivalent to preventing them from reaching the neutron detector 505. In this way, the neutrons that interact with the shield 512 are blocked or prevented from being detected by the neutron detector 505.

The shield 512 may be made from any suitable material for slowing or reflecting neutrons, such as a plastic like high density polyethylene (HDPE) or ultra-high molecular weight polyethylene (UHMW). Various combinations of a neutron moderator such as HDPE and neutron filter such as cadmium can act as the neutron shield as well.

The shield 512 may be positioned to interact with at least a portion of cosmogenic neutrons 201, 202, 203 propagating in a direction of the neutron detector 505. Depending on use, a user may wish to shield the neutron detector 505 from neutrons propagating from one or more sources or directions. For example, a user wishing to measure only the local area neutrons 203 may wish to shield the neutron detector 505 from wide area and overhead neutrons 202, 201. A user wishing to measure only wide area neutrons 202 may wish to shield the neutron detector 505 from local area and overhead neutrons 203, 201. A user wishing to measure only neutrons from an intermediate area may wish to shield the neutron detector 505 from a portion of local area neutrons 203 and a portion of wide area neutrons 202. A user wishing to reduce the noise floor of the cosmogenic neutron sensor 510 may wish to shield the neutron detector 505 from overhead neutrons 201 in combination with other shielding patterns.

The location and sizing of the shield 512 may be dependent on the size of the neutron detector 505, the height of the detector above the measurement surface 500, the size of the measurement surface 500, or some combination thereof. In one example, a shield 512 positioned to interact with local area neutrons 203 may be located below the neutron detector 505 and may be at least the size of the lower side of the detector 505. In one example, the shield 512 may extend past the lower side of the detector 505 to interact with neutrons from a greater distance away. For wide area sensing, the shield 512 may be somewhat larger than the lower side of the detector 505. The size of the shield 512 below may influence what percentage of neutrons from below are blocked. In another example, a shield 512 positioned to interact with wide area neutrons 202 may cover the sides of the neutron detector 505 not facing the measurement surface 500. In another example, a shield 512 positioned to interact with overhead neutrons 201 may be located above the neutron detector 505 and may be at least the size of the upper side of the detector 505. In one example, the shield 512 may extend past the upper side of the detector 501 to interact with neutrons from a greater angle above the detector 505.

FIG. 5A shows the shield 512 interacting with neutrons from many different potential sources. Cosmogenic neutrons 400 propagate down from space and toward the measurement surface 500. Overhead neutrons 201 reach the shield 512 and are slowed or deflected when interacting with the shield material. Cosmogenic neutrons 400 that reach the measurement surface 500 interact with hydrogen in the surface material and propagate upward toward the cosmogenic neutron sensor 510. Wide area neutrons 202 and local area neutrons 203 reach the shield 512 and are slowed or deflected when interacting with the shield material. In one example, neutrons that do not interact with the shield 512 reach the moderator and the neutron detector 505 and are counted. In this way, only neutrons from particular and desired sources are detected by the cosmogenic neutron sensor 510.

The feasibility of a shield 512 has been confirmed by field experiments and neutron transport modeling over areas with contrasting water content. One of the experiments was a transect across a water tank surrounded by soil obtained using a standard moderated detector shown in FIGS. 3 and 4 followed by the cosmogenic neutron sensor shown in FIG. 6, below. The results, shown in FIG. 7, below, show that the standard detector is highly sensitive to local neutrons, and thus is not a good wide-area detector, whereas the detector with neutron shield below has a much reduced sensitivity to local neutrons and thus is a good wide-area detector. Other operating examples are discussed below.

The cosmogenic neutron sensor 510 may include additional electronic components, such as a power source, communications interface, control hardware, and the like. For portable detectors 510, the power source may be a battery or solar power. The communications interface may allow a user to collect and retrieve neutron data from the cosmogenic neutron sensor 510. The communications interface may include communications hardware, such as data ports, antennas, and the like, and may be accessed by wired or wireless communication. The control hardware may allow a user to operate and troubleshoot the device.

FIGS. 5B-5E are illustrations of cosmogenic neutron sensors 510 in accordance with a first exemplary embodiment of the present disclosure.

Figure 5C:
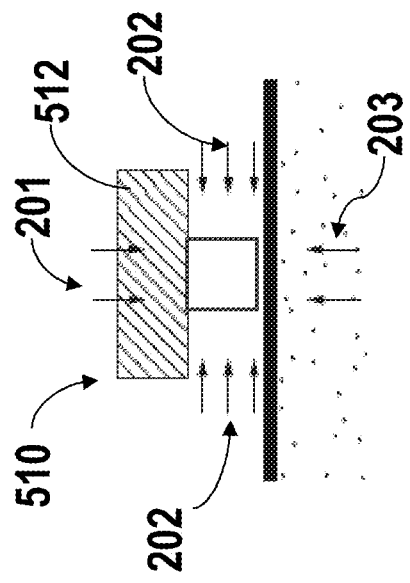
Figure 5E:
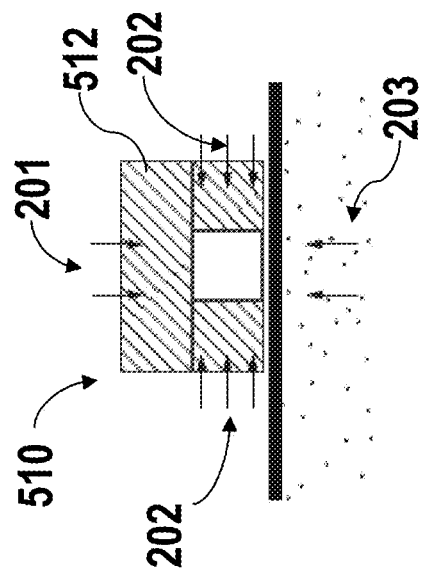
Figure 5B:
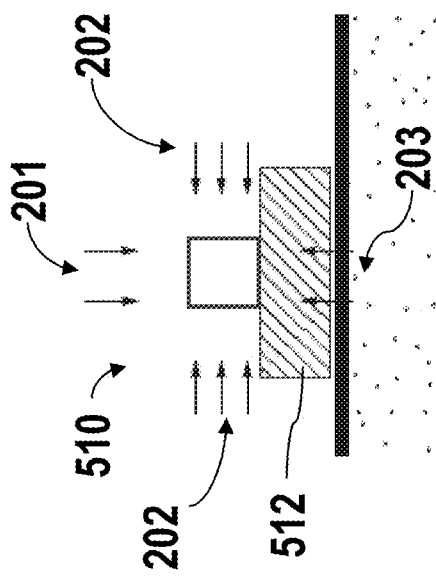

FIG. 5B shows a cosmogenic neutron sensor 510 with a wide area configuration. Neutrons 203 propagating from a local area below the cosmogenic neutron sensor 510 are blocked from reaching the neutron detector by a shield 512, while wide area neutrons 202 and overhead neutrons 201 reach the neutron detector.

FIG. 5C shows a cosmogenic neutron sensor 510 with a wide and local area configuration. Neutrons 201 propagating from overhead are blocked from reaching the neutron detector by a shield 512, while wide area nueutrons 202 and local area neutrons 203 reach the neutron detector.

Figure 5D:
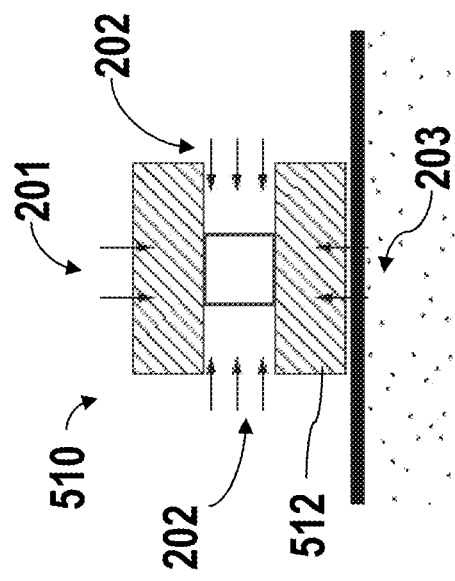

FIG. 5D shows a cosmogenic neutron sensor 510 with a wide area and noise reduction configuration. Neutrons 201, 203 propagating from overhead and from a local area below the cosmogenic neutron sensor 510 are blocked from reaching the neutron detector by a shield 512, while wide area neutrons 202 reach the neutron detector.

FIG. 5E shows a cosmogenic neutron sensor 510 with a local area and noise reduction configuration. Neutrons 201, 202 propagating from overhead and from a wide area below the cosmogenic neutron sensor 510 are blocked from reaching the neutron detector by a shield 512, while local area neutrons 203 reach the neutron detector.

Figure 6:
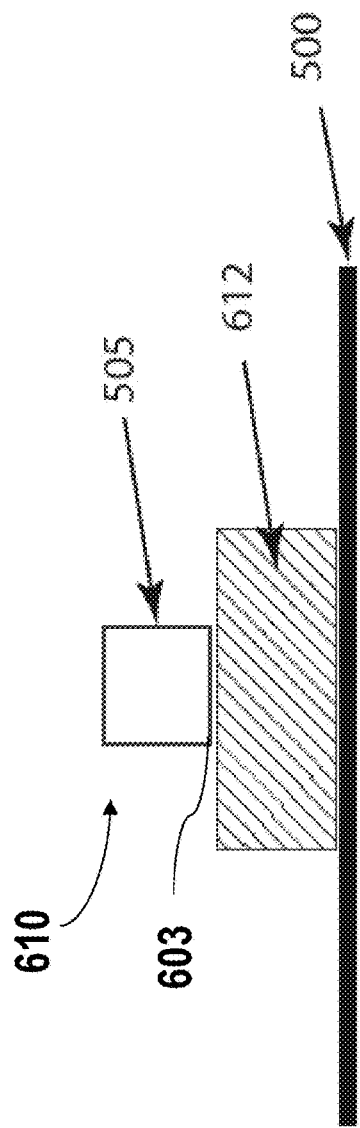
FIG. 6 is an illustration of a wide area cosmogenic neutron sensor, in accordance with the first exemplary embodiment of the present disclosure.

FIG. 6 is an illustration of a wide area cosmogenic neutron sensor 610, in accordance with the first exemplary embodiment of the present disclosure. The cosmogenic neutron sensor 610 may include a neutron detector 505. The neutron detector 505 may be orientable above a measurement surface 500. A neutron shield 612 may be positioned to interact with cosmogenic neutrons propagating from a local area of the measurement surface 500 below the neutron detector 505. FIG. 6 shows a cross-sectional illustration of the cosmogenic neutron sensor 610. The neutron detector 505 is oriented above a measurement surface 500. The neutron shield 612 is positioned on the neutron detector 505 at a bottom side of the detector 603. In one example, the neutron shield 612 may be made from HDPE and may be about 15 centimeters in thickness. In the example shown in FIG. 6, the neutron shield 612 covers the entirety of the bottom side of the detector 603 and extends outward past the neutron detector 505. This may provide shielding from the local area of the measurement surface 500 that is both directly below the neutron detector 505 and somewhat farther away. In another example, the neutron shield 612 may be smaller, covering only the bottom side of the detector 603.

This exemplary cosmogenic neutron sensor 610 may allow a user to measure only cosmogenic neutrons propagating from overhead and from a wide area of the measurement surface 500. This may allow the cosmogenic neutron sensor 610 higher sensitivity to wide area measurements, as the substantial contribution of neutrons from the local area of the measurement surface 500 will not be measured due to the neutron shield 612. In operation, this wide area-type cosmogenic neutron sensor 610 may be used at some height above the measurement surface 500 so as to detect neutrons from a broad area of the measurement surface 500.

Figure 7:
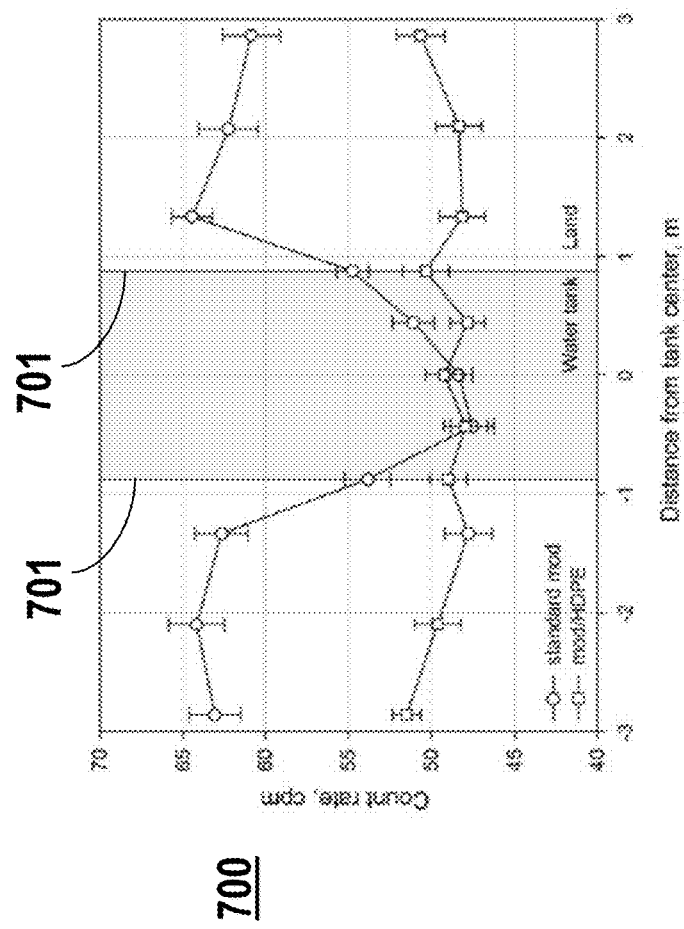
FIG. 7 is an exemplary transect graph of neutron intensity measured using the prior art moderated cosmogenic neutron sensor and the cosmogenic neutron sensor of FIG. 6.

FIG. 7 is an exemplary transect graph 700 of neutron intensity measured using the prior art moderated cosmogenic neutron detector and the cosmogenic neutron sensor 610 of FIG. 6. The two sensors were used to measure neutron intensity over a local area while being moved over a land measurement surface, over a water measurement surface, and back over a land measurement surface. The results of the prior art moderated cosmogenic neutron detector are shown with circular plot points as a function of position, while the results of the cosmogenic neutron sensor 610 of FIG. 6 are shown with square plot points as a function of position. The space between lines 701 indicates where the measurement surface was water. The space outside of lines 701 indicates where the measurement surface was land. The plot for the prior art sensor shows that it is sensitive to local area neutrons, and therefore shows a large change at the boundary between the water and the dry land. This is because the local area neutron contribution from a water measurement surface is lower than the local area neutron contribution from a land measurement surface. In contrast, the plot for the cosmogenic neutron sensor 610 shows no statistically relevant sensitivity to local neutrons. The neutron intensity count remains nearly constant as the cosmogenic neutron sensor 610 moves from land to water and back to land.

Figure 8:
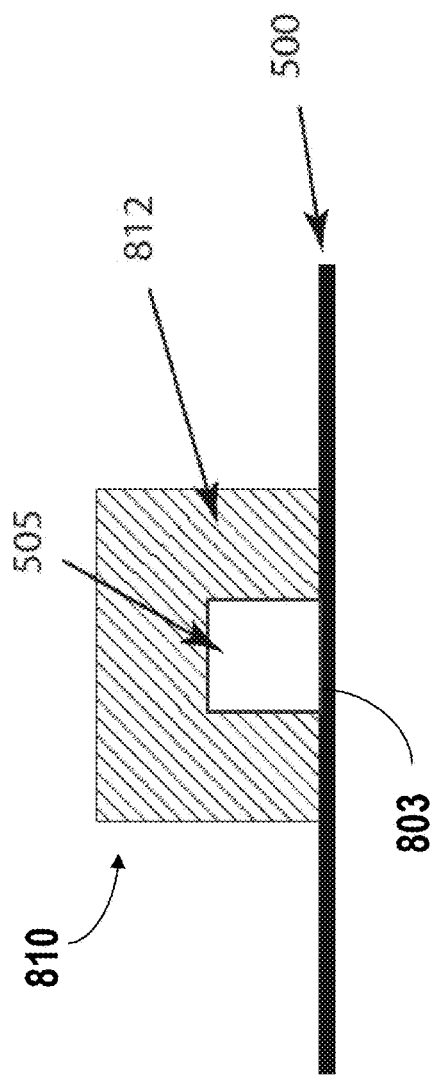
FIG. 8 is an illustration of a local area cosmogenic neutron sensor, in accordance with the first exemplary embodiment of the present disclosure.

FIG. 8 is an illustration of a local area cosmogenic neutron sensor 810, in accordance with the first exemplary embodiment of the present disclosure. The cosmogenic neutron sensor 810 may include a neutron detector 505 having a thermal neutron detector 501 inside. The neutron detector 505 may be orientable above a measurement surface 500. A neutron shield 812 may be positioned to interact with cosmogenic neutrons propagating from an area above the neutron detector 505 and a wide area below the neutron detector 505. The neutron shield 812 is positioned on the neutron detector 505 to shield the neutron detector 505 everywhere except for the bottom side of the detector 803. In one example, the neutron shield 812 may be made from HDPE and may be about 15 centimeters in thickness. In the example shown in FIG. 8, the neutron shield 812 covers the entirety of the detector 501 except for the bottom side of the detector 803. This includes a top side of the detector and horizontal sides of the detector. This may provide shielding from overhead and wide areas of the measurement surface 500.

This exemplary cosmogenic neutron sensor 810 may allow a user to measure only cosmogenic neutrons propagating from a local area of the measurement surface 500. This may allow the cosmogenic neutron sensor 810 higher sensitivity to local area measurements, as the substantial contribution of neutrons from the wide area of the measurement surface 500 and neutrons from overhead will not be calculated due to the neutron shield 812. In operation, this local area-type cosmogenic neutron sensor 810 may be used at a short height above the measurement surface 500 so as to detect neutrons from a specific surface area of the measurement surface 500.

Figure 9:
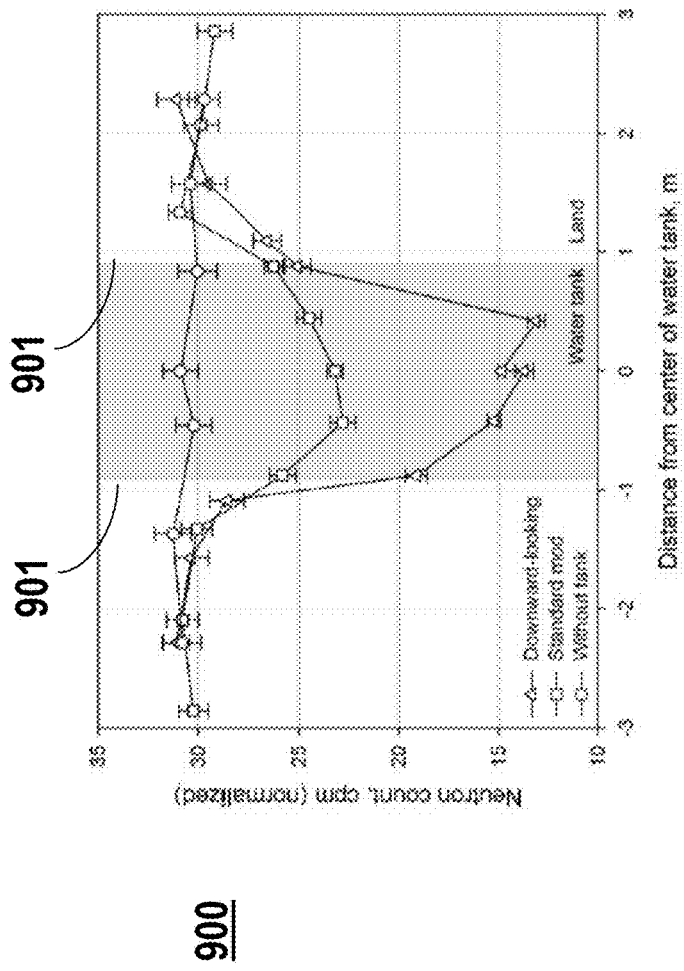
FIG. 9 is an exemplary transect graph of neutron intensity measured using the prior art moderated cosmogenic neutron sensor and the cosmogenic neutron sensor of FIG. 8.

FIG. 9 is an exemplary transect graph 900 of neutron intensity measured using the prior art moderated cosmogenic neutron detector and the cosmogenic neutron sensor 810 of FIG. 8. The feasibility of this cosmogenic neutron sensor 810 was confirmed by field experiments and neutron transport modeling over areas with contrasting water content. One was a transect across a water tank sunken into soil in which the prior art moderated detector was used, followed by the cosmogenic neutron sensor 810. As a control, the cosmogenic neutron sensor 810 was also used over the same soil area without the water tank present. The space between lines 901 indicates where the measurement surface was water, while the space outside lines 901 indicates where the measurement surface was land. The circle plot points show the baseline neutron intensities obtained by the cosmogenic neutron sensor 810 before the tank was installed. They indicate uniform soil moisture conditions along the land-water transect. The triangle plot points show measurements made with the cosmogenic neutron sensor 810. The cosmogenic neutron sensor 810 is sensitive to local neutrons and shows a change at the boundary between the water and the soil of nearly a factor of two. The square plot points show measurements made with the prior art moderated detector that sees both local neutrons and neutrons from far away. This is why the prior art moderated data show a smaller change between the water and the surrounding soil. The neutron contribution from far-away distances is greatly reduced by the cosmogenic neutron sensor 810, which detects and measures predominantly local area neutrons.

With the cosmogenic neutron sensor 810 at the measurement surface, its measurement footprint is similar to the physical size of the detector or its physical footprint, e.g., the length and width spatial dimensions of the detector. In the example shown in FIG. 9, this is approximately 0.5 meters. With the detector raised above the measurement surface, the measurement footprint increases significantly to the order of meters or tens of meters, depending on the height at which the cosmogenic neutron sensor 810 is placed. This is due to the fact that as the detector is raised above the measurement surface, the measurement footprint increases due to the increased angular area of neutron interaction below the detector, e.g., where the higher the detector is raised, a greater number of neutrons arriving on angular paths can be detected.

The results show that the prior art detector is capable of measuring only a small portion of the contrast between water and land, and thus is not a good local area detector. In contrast, the cosmogenic neutron sensor 810 has a much increased sensitivity to local neutrons and thus is a good small-area detector. This shows a much improved performance of the cosmogenic neutron sensor 810 with the neutron shield 812 around the entire detector 501 except at the bottom surface 803 in measuring local area neutrons. This measurement is substantially less affected by the wide area neutrons than measurements made with the prior art moderated detector. Essentially, the cosmogenic neutron sensor 810 measures substantially only the neutrons shown in FIG. 1A.

Figure 10B:
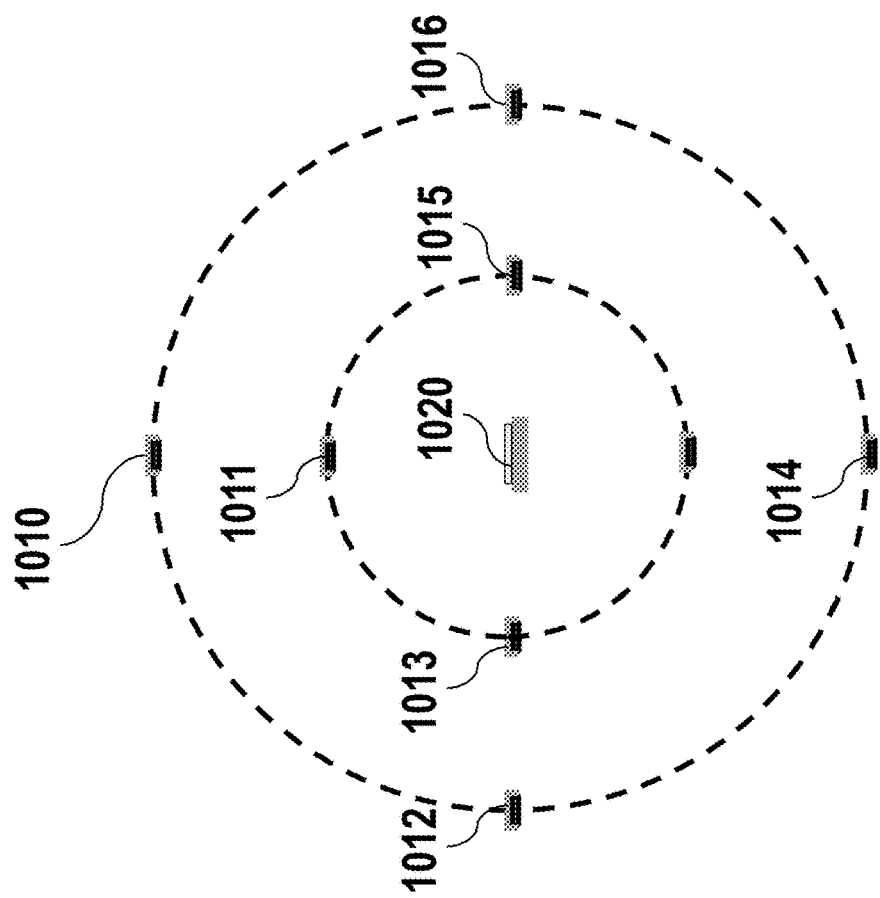
FIG. 10B is an exemplary illustration of a wide area calibration site.
Figure 10A:
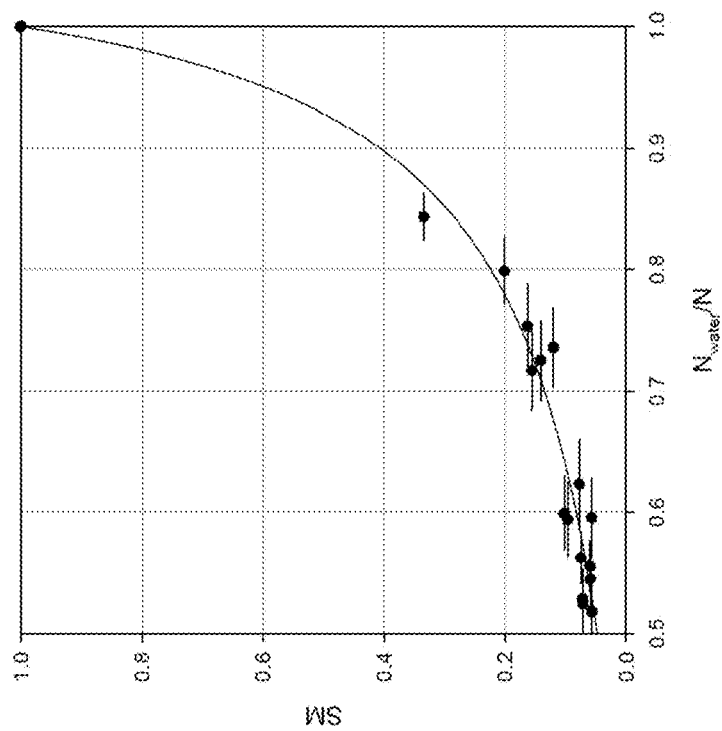
FIG. 10A is an exemplary graph of a calibration function measured using the cosmogenic neutron sensor of FIG. 8.

FIG. 10A is an exemplary graph 1000 of a calibration function measured using the cosmogenic neutron sensor of FIG. 8. The cosmogenic neutron sensor 810 was used to measure neutron intensity over solid surfaces with different soil water contents. The results were then normalized to the results of measured neutron intensity over water located in the same area, as in FIG. 9. The resultant curve was generally a match to the calibration curve of a standard prior art cosmogenic neutron sensor.

The feasibility of the cosmogenic neutron sensor to measure moisture across the full range of values, from dry soil to water, has been demonstrated by measurements over numerous sites with water content variable between a few percent by volume and 100% (water), assessed independently by taking soil samples, drying them in an oven, and computing water content from the water loss by drying. The results show a clear correlation between known soil water content and the neutron intensity, thus showing the feasibility of the detector.

FIG. 10B is an exemplary illustration of a wide area calibration site. To calibrate a wide area cosmogenic neutron sensor 1020, such as the one discussed in FIG. 6, above, a local area cosmogenic neutron sensor may be used to sample the moisture content in a number of local areas 1010-1016 within the wide area. The moisture content of the local areas 1010-1016 may be averaged or otherwise processed in order to calibrate the wide area cosmogenic neutron sensor 1020. This is discussed further in FIG. 17B, below.

Figure 11:
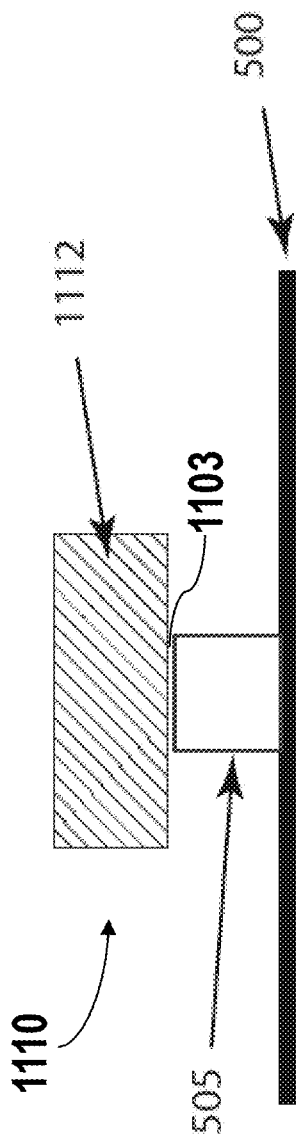
FIG. 11 is an illustration of a cosmogenic neutron sensor with an overhead neutron shield, in accordance with the first exemplary embodiment of the present disclosure.

FIG. 11 is an illustration of a cosmogenic neutron sensor 1110 with an overhead neutron shield 1112, in accordance with the first exemplary embodiment of the present disclosure. The cosmogenic neutron sensor 1110 may include a neutron detector 505. The neutron detector 505 may be orientable above a measurement surface 500. A neutron shield 1112 may be positioned to interact with cosmogenic neutrons propagating from an area above the neutron detector 505. The neutron shield 1112 is positioned on the neutron detector 505 to shield the neutron detector 505 from a top of the detector 1103. In one example, the neutron shield 1112 may be made from HDPE and may be about 15 centimeters in thickness. In the example shown in FIG. 11, the neutron shield 1112 covers the entirety of the top of the detector 1103 and extends further horizontally past the top of the detector 1103. This may provide shielding from overhead neutrons. In one example, the neutron shield 1112 may only cover the top of the detector 1103 without extending further, depending on the intended use of the cosmogenic neutron sensor 1110.

This exemplary cosmogenic neutron sensor 1110 may allow a user to measure only cosmogenic neutrons propagating from local and wide areas of the measurement surface 500. This may allow the cosmogenic neutron sensor 1110 higher sensitivity to these measurements, as the substantial contribution of neutrons from overhead will not be calculated due to the neutron shield 1112. Essentially, the unimportant neutrons contributing to the noise of the detector 1110 may be blocked.

Figure 12:
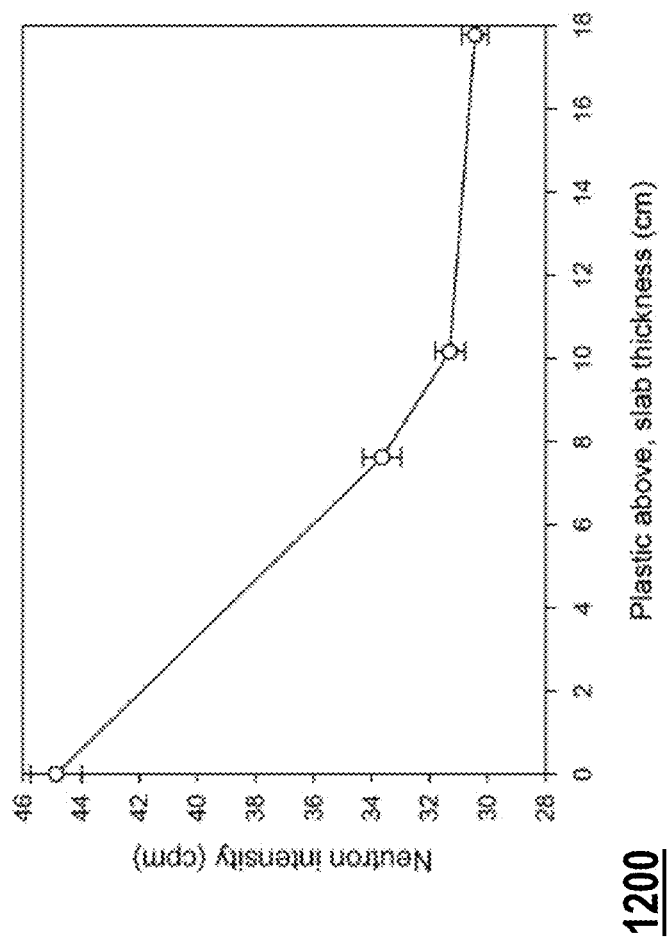
FIG. 12 is an exemplary graph of the neutron intensity as a function of neutron shield thickness measured using the cosmogenic neutron sensor of FIG. 11.

FIG. 12 is an exemplary graph 1200 of the neutron intensity as a function of neutron shield thickness measured using the cosmogenic neutron sensor 1110 of FIG. 11. Four neutron shields 1112 of increasing thickness were tested. The greatest decrease in neutron intensity is shown using shields of up to about 10 centimeters thick. Thus, a thickness of about 10 or more centimeters may be sufficient to block a reasonable number of overhead neutrons from reaching the neutron detector 505.

Figure 13A:
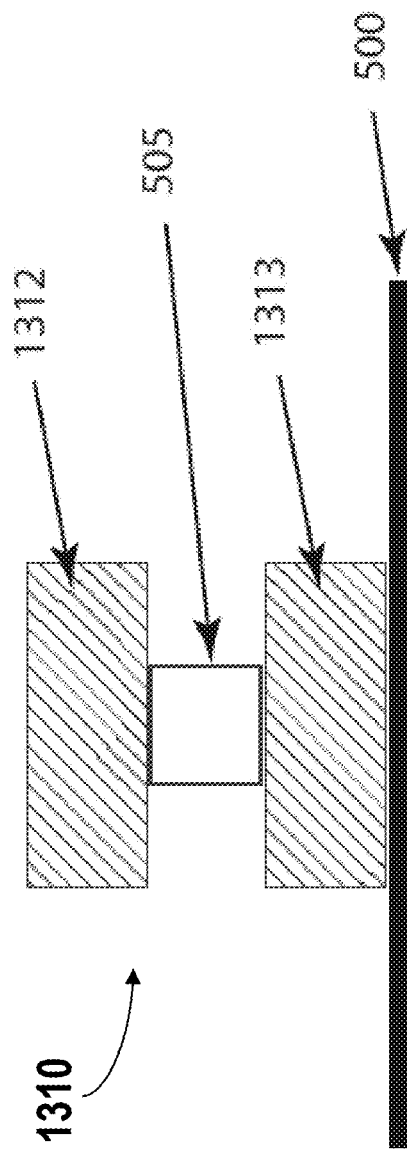
FIGS. 13A-13B are illustrations of wide area cosmogenic neutron sensors, in accordance with the first exemplary embodiment of the present disclosure.
Figure 13B:
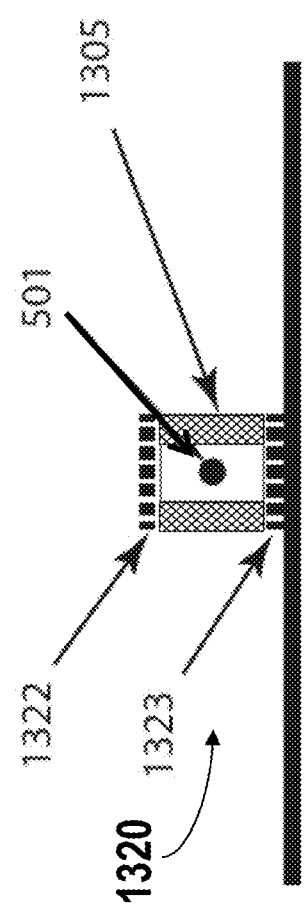

FIGS. 13A-13B are illustrations of wide area cosmogenic neutron sensors 1310, 1320, in accordance with the first exemplary embodiment of the present disclosure.

FIG. 13A shows a cosmogenic neutron sensor 1310 for detecting wide area neutrons. The cosmogenic neutron sensor 1310 may include a neutron detector 505. The neutron detector 505 may be orientable above a measurement surface 500. Neutron shields 1312, 1313 may be positioned on the neutron detector 505. Upper neutron shield 1312 may be positioned to interact with cosmogenic neutrons propagating from an area above the neutron detector 505. Lower neutron shield 1313 may be positioned to interact with cosmogenic neutrons propagating from a local area below the neutron detector 505. The neutron shields 1312, 1313 are positioned on the neutron detector 505 to shield the neutron detector 505 at a top and bottom of the detector. In one example, the neutron shield 1312 may be made from HDPE and may be about 15 centimeters in thickness. In the example shown in FIG. 13A, the neutron shields 1312, 1313 cover the entirety of the top and bottom of the neutron detector 505 and extend further horizontally past the neutron detector 505. This may provide shielding from overhead neutrons and local area neutrons below the neutron detector 505. In one example, the neutron shields 1312, 1313 may only cover the top and bottom of the neutron detector 505 without extending further, depending on the intended use of the cosmogenic neutron sensor 1310.

FIG. 13B shows a cosmogenic neutron sensor 1320 modified to weigh less than the cosmogenic neutron sensor 1310 of FIG. 13A. The cosmogenic neutron sensor 1320 may include a neutron detector 1305. The neutron detector 1305 may include a neutron detector 501 and a moderating material located around a portion of the neutron detector 501. The moderating material, or moderator, may be positioned to moderate cosmogenic neutrons propagating from a wide area of the measurement surface 500 below the neutron detector 505. Portions of the neutron detector 505 that will be shielded may not have the moderating material in order to reduce the detector 1305's weight. The neutron detector 505 may be orientable above a measurement surface 500. Neutron shields 1322, 1323 may be positioned on the neutron detector 505. The neutron shields 1322, 1323 may be cadmium or a like material, and the size of the shields 1322, 1323 may cover only the top and bottom of the neutron detector 505. This may allow the cosmogenic neutron sensor 1320 to be smaller and more lightweight than the detector described relative to FIG. 13A.

Figure 14:
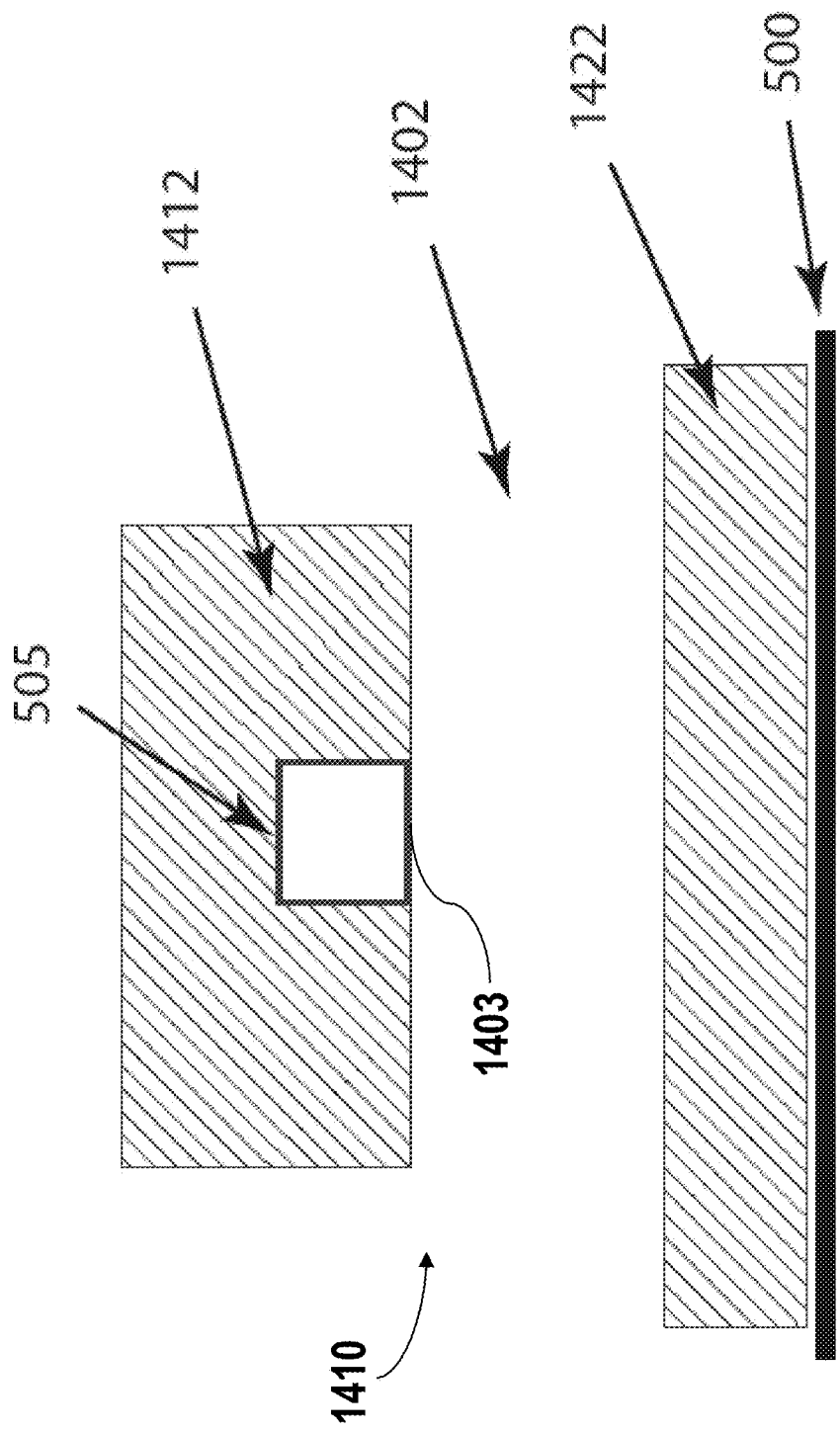
FIG. 14 is an illustration of an intermediate area cosmogenic neutron sensor, in accordance with the first exemplary embodiment of the present disclosure.

FIG. 14 is an illustration of an intermediate area cosmogenic neutron sensor 1410, in accordance with the first exemplary embodiment of the present disclosure. The cosmogenic neutron sensor 1410 may include a neutron detector 505. The neutron detector 505 may be orientable above a measurement surface 500. The cosmogenic neutron sensor 1410 may have a neutron shield 1412 on the neutron detector 505 and a neutron shield 1422 below the neutron detector 505. The neutron shield 1412 on the neutron detector 505 may interact with neutrons propagating from overhead and from a portion of a wide area below the neutron detector 505. The neutron shield 1422 may interact with neutrons propagating from a portion of a local area below the neutron detector 505. The bottom side of the thermal neutron detector 1403 may not be directly covered by the neutron shield 1412, 1422. An air gap 1402 may separate the neutron detector 505 and the lower neutron shield 1422. The neutron shield 1412, 1422 may be positioned to allow cosmogenic neutrons propagating from an intermediate area of the measurement surface 500 below the neutron detector 505, as the neutron shield elements 1412, 1422 are spaced apart vertically. The neutron shield 1412, 1422 reduces the local area neutron contribution, wide area neutron contribution, and overhead neutron contribution. However, neutrons propagating toward the neutron detector 505 from an intermediate distance are not blocked from hitting the detector 501. The scale of observation can be controlled by changing the size of the air gap 1402 between the lower neutron shield 1422 and the upper neutron shield 1412, as well as by adjusting the sizes of the neutron shields 1412, 1422.

Figure 15:
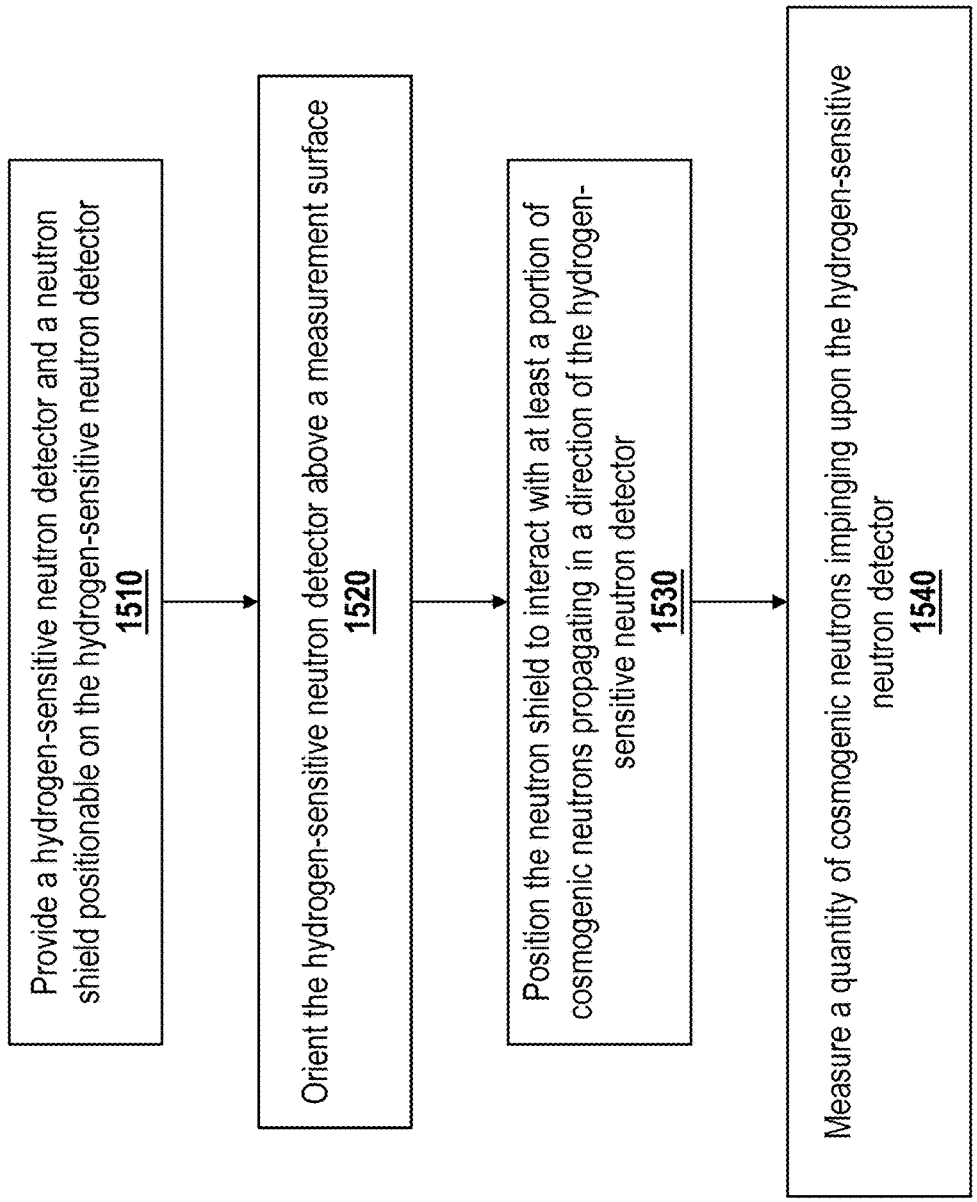
FIG. 15 is a flow chart showing a method for detecting cosmogenic neutrons, in accordance with the first exemplary embodiment of the present disclosure.

FIG. 15 is a flow chart showing a method for detecting cosmogenic neutrons, in accordance with the first exemplary embodiment of the present disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

Step 1510 includes providing a neutron detector and a neutron shield positionable on the neutron detector. The neutron detector and neutron shield may be the same neutron detector and neutron shield described relative to FIGS. 5-14, above.

Step 1520 includes orienting the neutron detector above a measurement surface. The measurement surface may be any desired measurement surface, including land, water, urban construction, and the like. The neutron detector may be oriented above the measurement surface by any suitable means. In one example, the neutron detector may be placed on a number of legs or a stand. In another example, the neutron detector may be a handheld device that is oriented above the measurement surface by a user of the device. In another example, the neutron detector may be attached to a vehicle, such as an automobile, airplane, or drone. The vehicle may hold the neutron detector above the measurement surface while also moving the neutron detector about the measurement surface. This may be particularly helpful for local area measurements made over a large area. In another example, the neutron detector may be attached to an aircraft, drone, satellite, tower, or tall building.

Step 1530 includes positioning the neutron shield to interact with at least a portion of cosmogenic neutrons propagating in a direction of the neutron detector. The neutron shield may be positioned in one or more places on the neutron detector in order to interact with cosmogenic neutrons propagating from one or more particular directions. For example, the neutron shield may be positioned on a top or upper portion of the neutron detector in order to interact with overhead neutrons. The neutron shield may be positioned on a bottom or lower portion of the neutron detector in order to interact with local area neutrons propagating from below the neutron detector. The neutron shield may be positioned on or around a side portion of the neutron detector in order to interact with wide area neutrons propagating from below the neutron detector. The positions of the shields may be combined as well. A neutron shield may be positioned on a top portion of the neutron detector and a bottom portion of the neutron detector in order to interact with cosmogenic neutrons propagating from overhead and from a local area below the neutron detector. Only a portion of a side of the neutron detector may be covered by the neutron shield. Any other combinations and permutations of the neutron shield location may be considered within the scope of this disclosure.

Step 1540 includes measuring a quantity of cosmogenic neutrons impinging upon the neutron detector. For stationary sensors, measurements may be made over the course of several minutes to one hour. For mobile sensors, measurements may be made over the course of several seconds to several minutes. Software may record the various measurements and process them to convert a neutron count rate to a moisture content value.

The method may further include any other features, components, or functions disclosed relative to any other figure of this disclosure.

Figure 16:
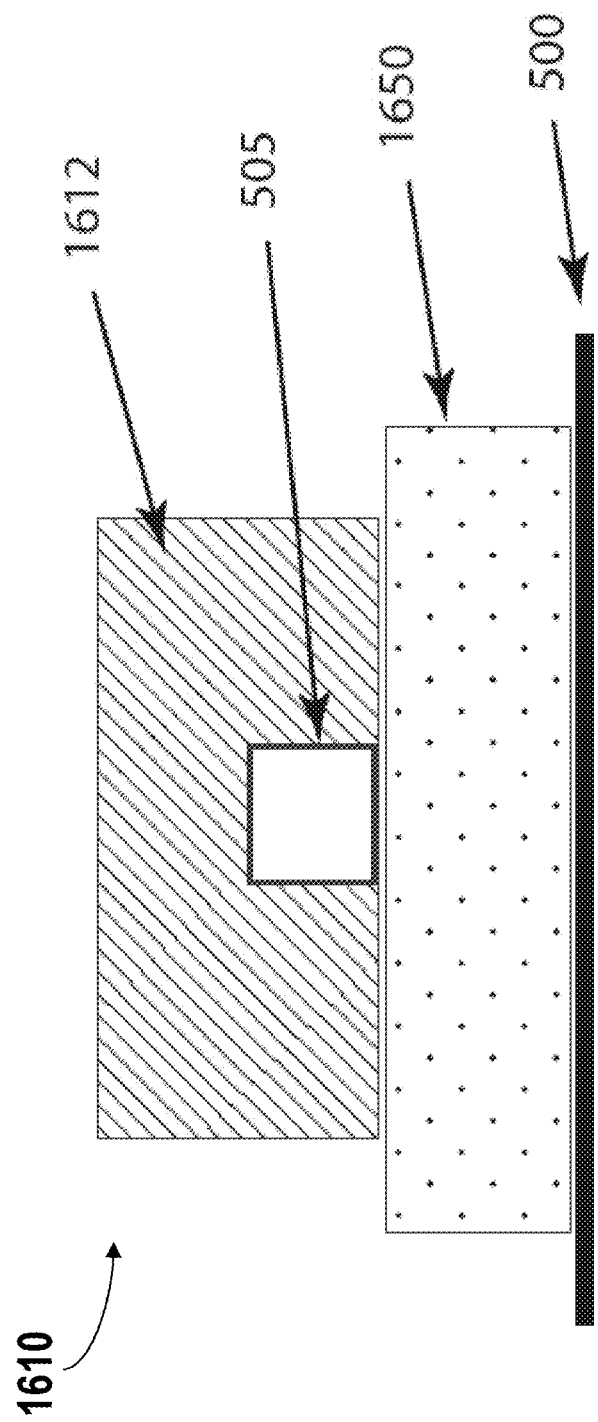
FIG. 16 is an illustration of the cosmogenic neutron sensor in use during calibration, in accordance with a second exemplary embodiment of the present disclosure.

FIG. 16 is an illustration of the cosmogenic neutron sensor 1610 in use during calibration, in accordance with a second exemplary embodiment of the present disclosure. The cosmogenic neutron sensor 1610 may be the local area-type detector discussed relative to FIG. 8, above. The cosmogenic neutron sensor 1610 may include neutron detector 505 having a neutron shield 1612 positioned to interact with neutrons propagating from a wide area of the measurement surface 500 below the neutron detector 505. In one example, the neutron shield 1612 may also be positioned to interact with neutrons propagating from above the measurement surface 500 so as to decrease the noise of the cosmogenic neutron sensor 1610. Thus, the cosmogenic neutron sensor 1610 may primarily measure the intensity of neutrons propagating from a local area below the neutron detector 505.

The cosmogenic neutron sensor 1610 may be calibrated by using the detector 1610 to record specific measurements, then calculating a calibration curve. This is described further in FIGS. 17A-17B, below. FIG. 16 shows the cosmogenic neutron sensor 1610 oriented above a first measurement surface 500, which may be a body of water, as well as above a second measurement surface 1650, which may be a constant hydrogen content surface. The constant hydrogen content surface material may be one or more material with precisely engineered hydrogen content. For example, the material may be a combination of mineral grains mixed with water to achieve the specific hydrogen content. In another example, a material may be fabricated by combining particular amounts of mineral grains, for example, quartz sand, with amounts of HDPE particles, to make a homogenous mixture that can be pressed or melted into a solid material. The hydrogen content of the material will remain constant over time; thus, the material can be used to calibrate the cosmogenic neutron sensor 1610. Multiple different materials representing a full range of hydrogen content or moisture content may be used to calibrate a cosmogenic neutron sensor 1610 over the range.

FIG. 17A is a flow chart showing a method of calibrating a local area cosmogenic neutron sensor for soil moisture detection, in accordance with a second exemplary embodiment of the present disclosure. Traditionally, a calibration function for the standard cosmogenic soil moisture probe is obtained using measured neutron intensity and independently measured soil moisture to calculate a parameter. Two or more calibrations at different soil moisture values are needed to define the curve, and the calibration measurements must be performed by heating the samples in an oven and measuring the mass of water removed in order to obtain the moisture content of the soil. This can be an inconvenient, labor-intensive process. The method of calibrating a local area cosmogenic neutron sensor described herein allows calibration tests to be made and verified from within the cosmogenic neutron sensor. The objective of the method is to find the relationship between local area soil moisture and local area neutron intensity. In order to do that, neutron intensity may be measured at a number of local area sites with varying soil moisture contents or using a number of artificial materials with varying, but known, hydrogen content. The resulting calibration function may be of the form: N=f(SM), where N is neutron intensity, and f(SM) is a function of the soil moisture.

Step 1710 includes providing a neutron detector and a neutron shield positioned to interact with cosmogenic neutrons propagating from a wide area of a measurement surface below the neutron detector. In one example, the neutron shield may also be positioned to interact with cosmogenic neutrons propagating from above the neutron detector. In other words, the cosmogenic neutron sensor may be a local area-type detector for measuring neutrons propagating toward the neutron detector from a local area below the detector.

Step 1720 includes orienting the neutron detector above a first measurement surface. This may be done as described in FIG. 15, above. The first measurement surface may generally be a body of water. The neutron detector may be oriented at a suitable height above the first measurement surface to make an accurate measurement.

Step 1730 includes measuring the neutron intensity of the first measurement surface. The neutron intensity may be recorded and stored, either onboard the cosmogenic neutron sensor, or on connected memory. Step 1730 may also include measuring the moisture content of the first measurement surface using an alternative method, such as oven drying, capacitive, resistive, core sampling method, and the like. This may provide verification for the measured neutron intensity of the first measurement surface as a function of the soil moisture. If the moisture content of the first measurement surface is already known—for instance, if the first surface is water or an artificial surface having a known moisture content—then using an alternative method to measure the moisture content of the first measurement surface may be redundant.

Step 1740 includes calibrating a cosmogenic neutron sensor based on the measured neutron intensity of the first measurement surface and at least one additional data point. In one example, the at least one additional data point may be a measurement of the neutron intensity from at least a second measurement surface. The at least second measurement surface must be a different measurement surface than the first measurement surface. The second measurement surface may have a different moisture content from the first measurement surface. Third and subsequent measurements may have different levels of moisture content as well. The first and subsequent measurements of neutron intensity at the first and subsequent measurement surfaces may be correlated to first and subsequent moisture content values, either as described above or using other correlation methods. For instance, a first measurement may be correlated with a first moisture content value using an alternative measurement method. Subsequent measurements may be correlated with subsequent moisture content values using the same alternative measurement method. This may be repeated a number of times in order to provide a sufficient amount of data to define a calibration curve. The moisture content values may be used to define the calibration curve as a function of moisture content.

When the at least one additional data point is measured from at least a second measurement surface, calibrating may include measuring the neutron intensity of the at least second measurement surface. In one example, the first measurement surface may be a body of water, and a second measurement surface may be a constant hydrogen content surface. The body of water may provide a calibration measurement for a measurement surface with 100% moisture content, while the constant hydrogen content surface may provide a calibration measurement for a measurement surface with a specific and known moisture content. Additional measurements may be made with constant hydrogen content surfaces of other specific and known moisture contents. For example, the first measurement may be with a surface having 100% moisture content, while a second may be made with a surface having 75% moisture content, and a third may be made with a surface having 10% moisture content.

Calibrating may further include defining a calibration curve based on the first and at least second measurements. The calibration curve may be defined based on any suitable analytical techniques, depending on the number of measurements, the accuracy desired, and the intended use of the cosmogenic neutron detector. For example, regression analysis may be combined with the double exponential curve of the radial sensitivity function to calculate the calibration parameters of two or more measurements. The cosmogenic neutron sensor may be calibrated based on the defined calibration curve.

In one example, the at least one additional data point may be a known calibration curve for the cosmogenic neutron sensor. For instance, if a calibration curve is already known, then the cosmogenic neutron sensor may only require a single measurement of neutron intensity over a surface. The single measurement may be correlated to a moisture content value and fit to the known calibration curve, and the cosmogenic neutron sensor may be calibrated according the to fit.

In one example, the cosmogenic neutron sensor may be oriented on a soil surface, wherein the bottom of the cosmogenic neutron sensor touches the soil surface. The neutron intensity of the first measurement surface may be measured to a desired precision. The cosmogenic neutron sensor may be removed, and soil samples from the measured area may be collected at depths between 0 centimeters and 30 centimeters to allow for gravimetric water content measurements. At least one additional data point may be obtained from at least a second measurement. At least one of the additional data points may be a measurement made over a water surface. The moisture content of the soil samples may be determined by an alternative method. A calibration curve may then be defined based on the measurements of the neutron intensities and the corresponding measurements of the moisture content of the local areas.

FIG. 17B is a flow chart showing a method of calibration of a wide area cosmogenic neutron sensor for soil moisture detection, in accordance with the second exemplary embodiment of the present disclosure.

Step 1750 includes determining at least two local area calibration functions, each determined by: providing a hydrogen-sensitive neutron detector and a neutron shield positioned to interact with cosmogenic neutrons propagating from a wide area of a measurement surface below the hydrogen-sensitive neutron detector; orienting the hydrogen-sensitive neutron detector above a first measurement surface; and calibrating a cosmogenic neutron sensor based on the defined measured neutron intensity of the first measurement surface and at least one additional data point to produce a local area calibration data point.

In one example, a local area cosmogenic neutron sensor may be used as described in steps 1710-1740. The first measurement surface may be a local area portion of a wide area measurement surface. The at least one additional data point may be a measurement from a second surface, which may be a different local area having a different moisture content or a material having a known moisture or hydrogen content. Any additional measurements may be made from yet different local areas of the measurement surface. The at least one additional data point may alternatively be a known calibration curve for the cosmogenic neutron sensor. The cosmogenic neutron sensor may be calibrating based on the measured neutron intensity of the first measurement surface and the at least one additional data point. This may produce a local area calibration function.

The local area calibration function may be determined for at least two local area points. As shown in FIG. 10B, local area calibration functions may be determined from a number of local areas within a wide area to ultimately be measured.

Step 1760 includes calibrating a wide area cosmogenic neutron sensor based on the at least two determined local area calibration functions and a weighting function. The wide area cosmogenic neutron sensor may be a wide area cosmogenic neutron sensor described herein, or it may be a prior art cosmogenic neutron sensor. In one example, the weighting function may include a spatial sensitivity function. The wide area calibration curve may be defined based on an average of the at least two local area calibration functions, as this may indicate the average moisture content over the wide area. This calibration curve may be used to calibrate a wide area cosmogenic neutron sensor for the wide area measurement surface.

In one example, the method may be performed using a local area cosmogenic neutron sensor and a wide area cosmogenic neutron sensor. The local area cosmogenic neutron sensor may be used to calibrate the wide area cosmogenic neutron sensor. The wide area cosmogenic neutron sensor may be placed above a first surface. In one example, this point may be the center of a wide area measurement surface. The wide area measurement surface may be a circular area roughly 400 meters in diameter. The wide area cosmogenic neutron sensor may be used to make a wide area measurement for the remaining duration of the method. The local area cosmogenic neutron sensor may be used to measure the neutron intensity, and subsequently, the moisture content, of a local area within the wide area measurement surface. A local area moisture content measurement may be made for a different local area within the wide area measurement surface. A number of local area measurements may be made in order to sufficiently compute an accurate and precise average soil moisture over the wide area measurement surface. In one example, this may be 10 or more local area measurements. Preferably, this will be at least 18 local area measurements, depending on the side of the wide area measurement surface.

The average wide area soil moisture may be determined from the local area measurements. The wide area cosmogenic neutron sensor may finish making the wide area neutron intensity measurement. An average neutron intensity for the wide area may be determined for the measurement interval. A calibration function may be determined based on the average local area moisture measurements and the average neutron intensity for the wide area. This calibration function may be weighted by a weighting function, which may be the spatial or radial sensitivity function.

In one particular example, a wide area cosmogenic neutron detector may be used to make a measurement. A local area cosmogenic neutron detector may be calibrated as discussed relative to FIG. 17A, above. The local area cosmogenic neutron detector may be used to measure neutron intensity at 18 sites within a 200 meter radius of the wide area cosmogenic neutron sensor. The local area neutron intensity measured at the 18 sites may be converted to moisture level values using the calibration function determined during the local area cosmogenic neutron detector calibration. A few grams of soil from each of the local area sites may be collected. A soil composite may be made by mixing 1-2 grams of each of the collected soil samples together to form a relatively homogenous mixture. The lattice water or hydrogen content of the soil composite may be measured. The soil organic carbon of the soil composite may be measured. The average moisture content may be determined from the above measurements. A calibration function for the wide area cosmogenic neutron sensor may be determined, and the sensor may be calibrated.

The usual calibration of such sensors involves taking numerous soil samples and measuring their hitherto unknown water content in the laboratory. The number of samples has to be sufficient to capture the spatial variability of soil moisture; Zreda et al. (2012) suggested taking 108 samples. The samples are dried in laboratory oven and their water content is calculated from the difference between wet soil mass and its dry mass. The process is laborious, expensive and at many locations difficult or impossible to conduct because of the presence of stones or rock outcrops in the soil. The new example above uses the local area cosmogenic neutron sensor to replace sampling and processing of soil. The measured local neutron intensities taken at many points inside the wide area measurement footprint are combined to produce an average value over the wide area sensor's measurement footprint. That value is used to calculate the calibration parameters.

Figure 18:
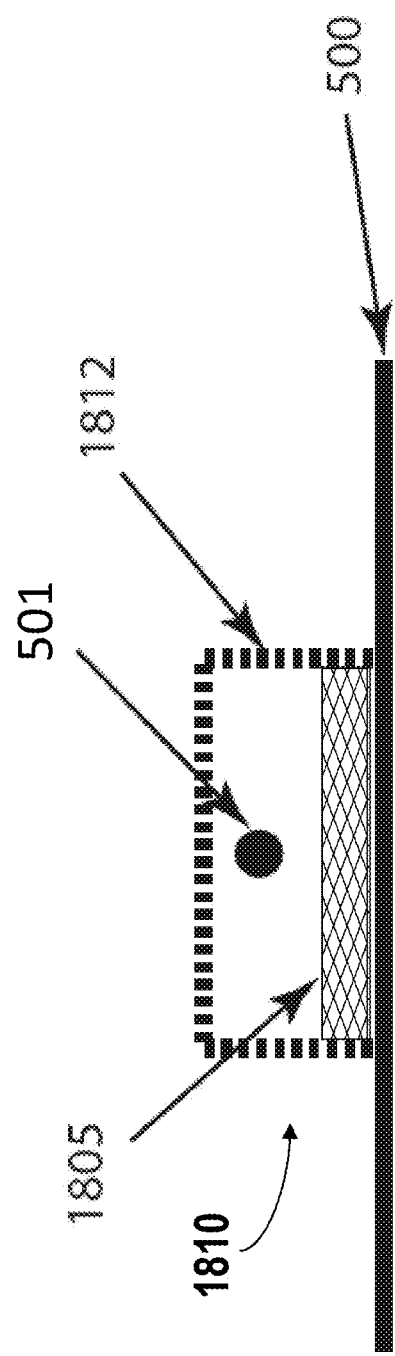
FIG. 18 is an illustration of a cosmogenic neutron sensor having overhead and wide area cadmium neutron shields, in accordance with the first exemplary embodiment of the present disclosure.

FIG. 18 is an illustration of a cosmogenic neutron sensor 1810 having overhead and wide area cadmium neutron shields 1812, in accordance with the first exemplary embodiment of the present disclosure. The cosmogenic neutron sensor 1810 may include a neutron detector 501, which may be the same as the neutron detector 301 shown in FIG. 3B, above. Moderating material 1805 may be positioned on the neutron detector 501 and at a bottom portion of the neutron detector 501. The moderating material 1805, or moderator, may be positioned to moderate cosmogenic neutrons propagating from a local area of the measurement surface 500 below the neutron detector 501. A cadmium neutron shield 1812 may be positioned on the neutron detector 501 to interact with neutrons propagating from above the neutron detector 501 and from a wide area of the measurement surface 500 below the neutron detector 501. The incorporation of a cadmium neutron shield 1812 in place of additional moderating material 1805 around the top and sides of the cosmogenic neutron sensor 1810 may cause the cosmogenic neutron sensor 1810 to weigh less than other examples discussed herein. This may be particularly useful for cosmogenic neutron sensors 1810 for use in airplanes, drones, satellites, and other aerial vehicles, as a reduced payload may be required for the cosmogenic neutron sensor 1810 to be able to be used with these vehicles.

This is a cadmium improvement of the prior art moderated detector discussed in FIGS. 3A-3B, above. The moderator that is on all sides of the detectors in FIG. 3B may be reduced to one moderator slab 1805 placed below the neutron detector 501, and surrounded by a cadmium sheet 1812. Epithermal neutrons coming from below enter the space enclosed by cadmium 1812, undergo moderation in the moderator 1805 and become thermal neutrons that are counted by the neutron detector 501. Epithermal neutrons coming from all other directions enter the space enclosed by cadmium 1812, reflect off the moderator slab 1805, become thermalized, and are counted by the neutron detector 501. The main advantage of this example is a significant reduction of mass of the instrument, which is important in aerial neutron sensing using drones where payload is a limiting factor.

Figure 19:
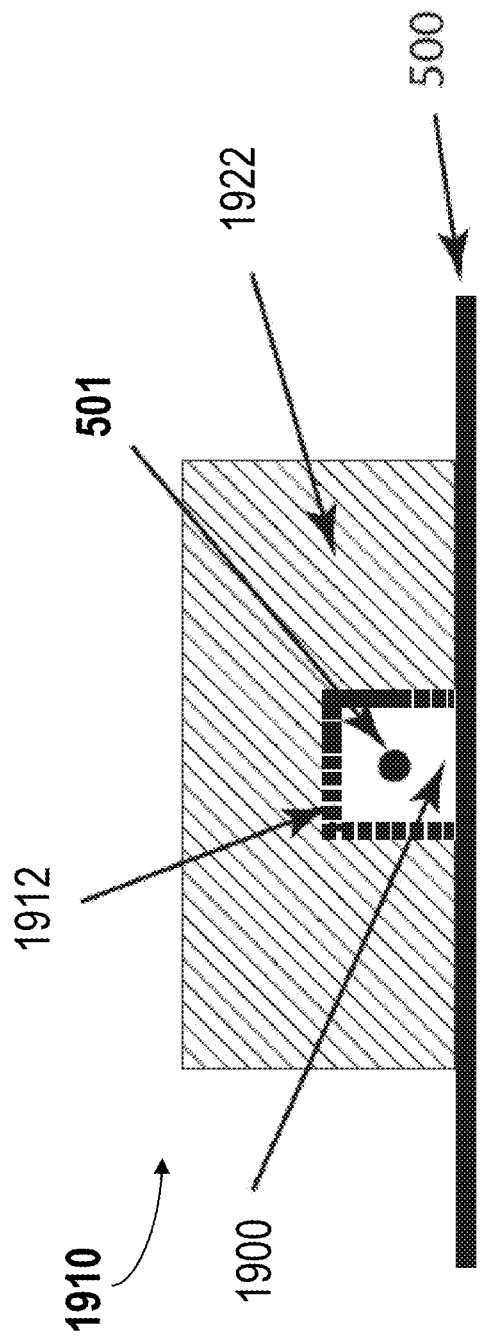
FIG. 19 is an illustration of a local area cosmogenic neutron sensor with a neutron shield and a cadmium foil layer, in accordance with the first exemplary embodiment of the present disclosure.

FIG. 19 is an illustration of a local area cosmogenic neutron sensor 1910 with a neutron shield 1922 and a cadmium foil layer 1912, in accordance with the first exemplary embodiment of the present disclosure. The cosmogenic neutron sensor 1910 may include a neutron detector 501 oriented above a measurement surface 500. A layer of cadmium foil 1912 may be positioned around the neutron detector 501, leaving a gap space 1900. The gap space 1900 may contain air, or it may be a vacuum. A neutron shield 1922 may be positioned on the layer of cadmium foil 1912. The cadmium foil and neutron shield 1912, 1922 may be positioned to interact with neutrons propagating from overhead and from a wide area of the measurement surface 500 below the neutron detector 501.

Figure 20:
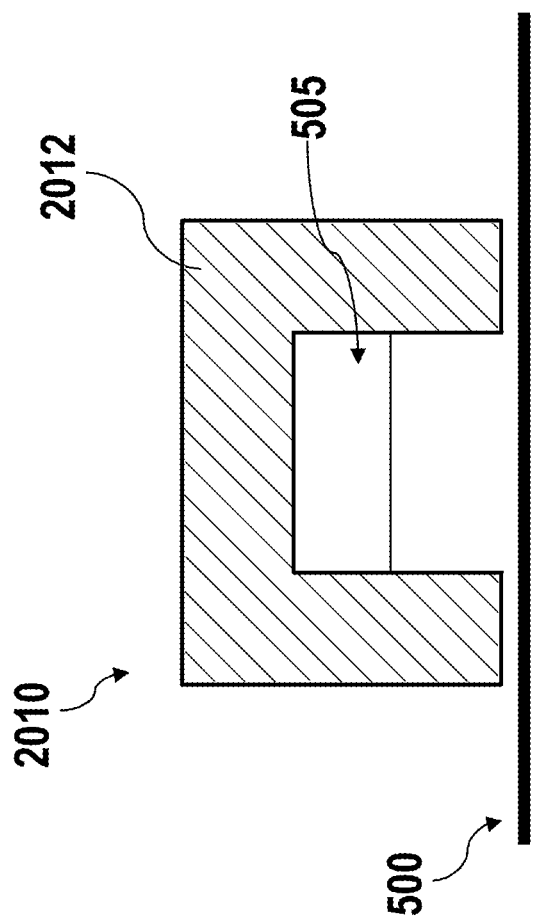
FIG. 20 is an illustration of a local area cosmogenic neutron sensor with a skirt-style neutron shield, in accordance with the first exemplary embodiment of the present disclosure.
Figure 21A:
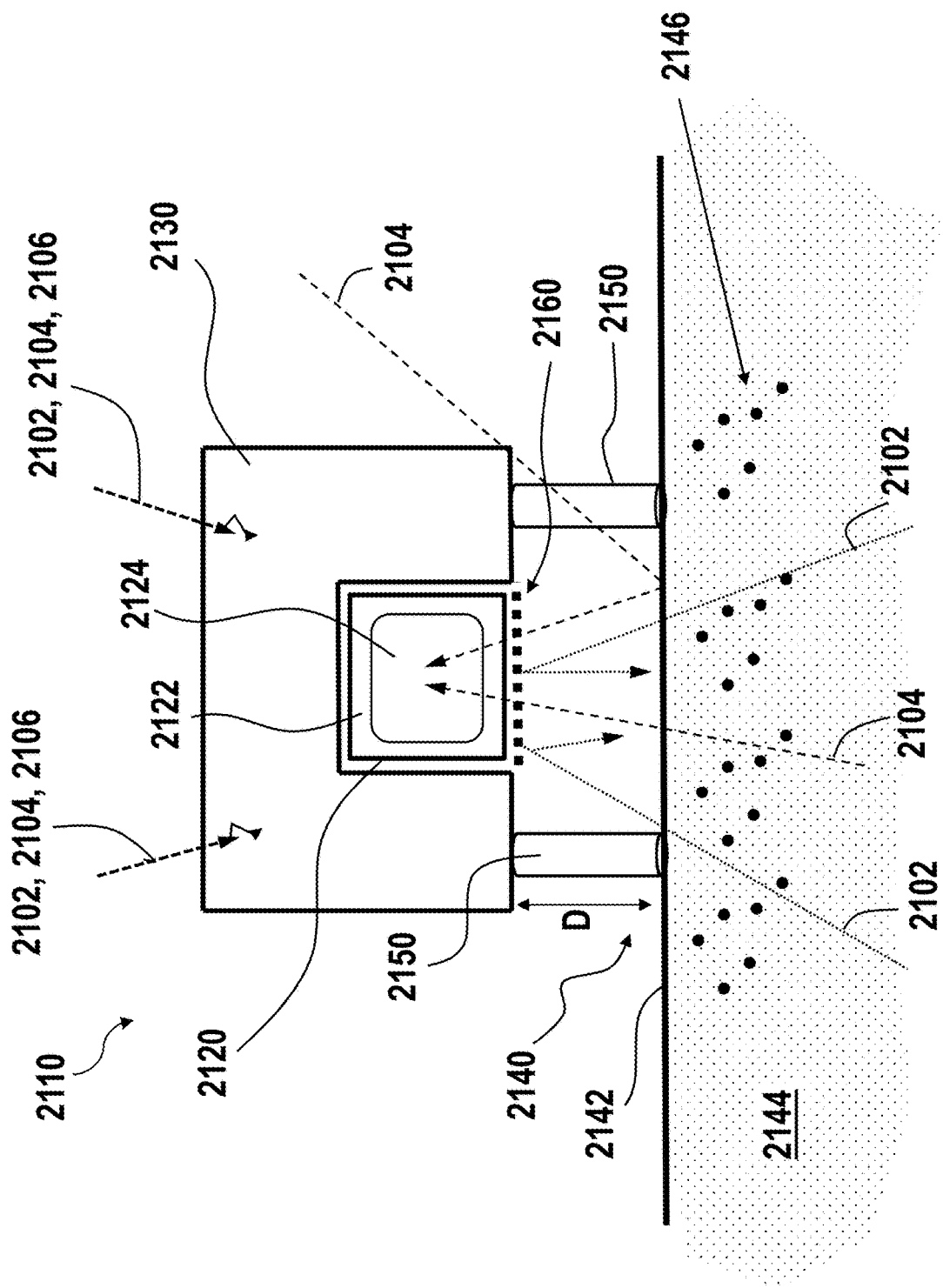
FIGS. 21A-21B are illustrations of a local area cosmogenic neutron sensor with a thermal neutron shield to improve signal-to-noise ratio and signal contrast, in accordance with the first exemplary embodiment of the present disclosure.
Figure 21B:
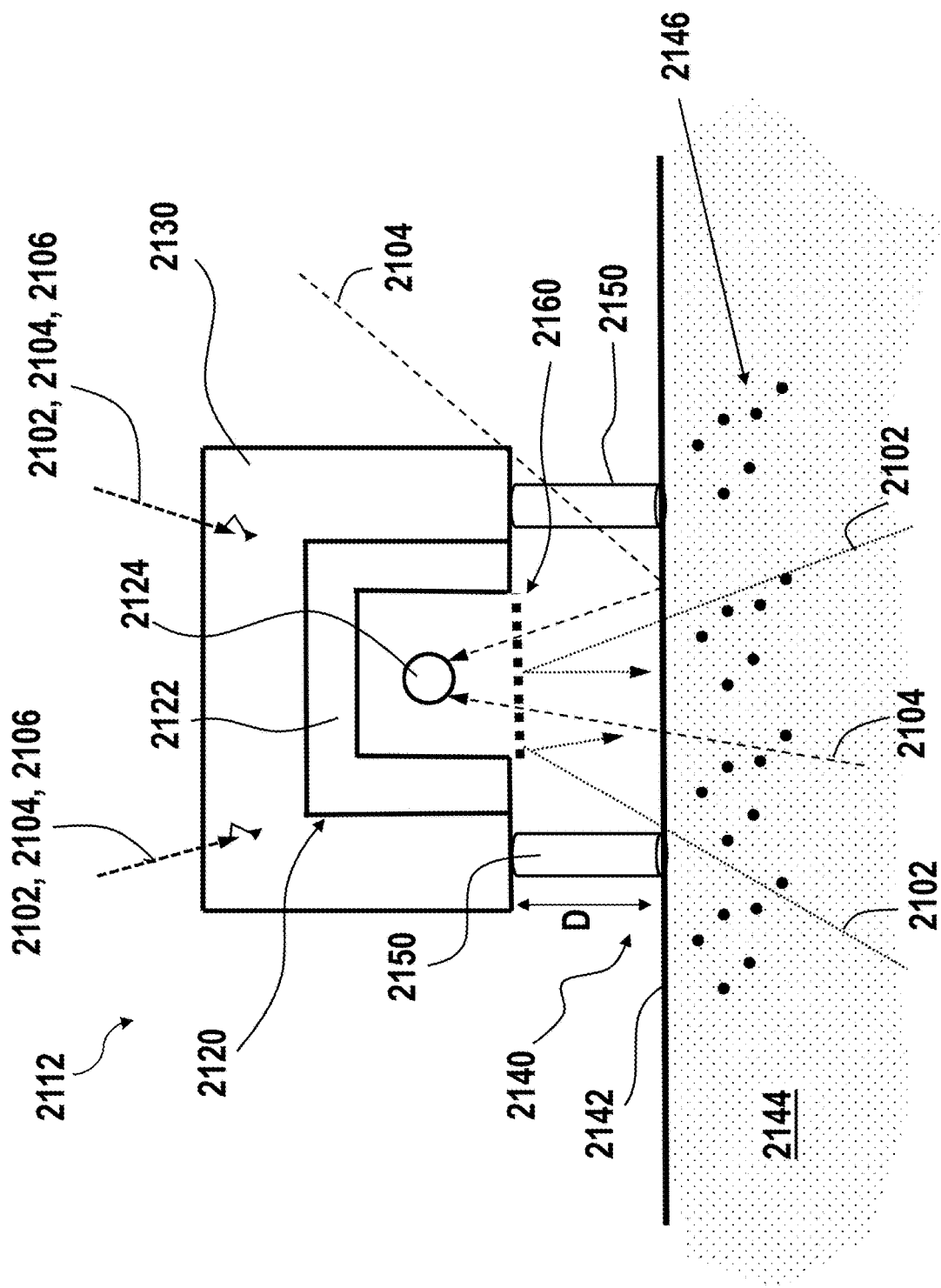

FIG. 20 is an illustration of a local area cosmogenic neutron sensor 2010 with a skirt-style neutron shield 2012, in accordance with the first exemplary embodiment of the present disclosure. The local area cosmogenic neutron sensor 2010 may include a neutron detector 501 positioned above a measurement surface 500. A skirt-style neutron shield 2012 may be positioned on the neutron detector 501 to interact with overhead and wide area neutrons. The sides of the neutron shield 2012 may extend vertically below the neutron detector 501 toward the measurement surface 500. This may enhance the neutron shield 2012's effectiveness in blocking wide area neutrons by narrowing the cosmogenic neutron sensor 2010's local area measurement footprint. In turn, the resolution of the cosmogenic neutron sensor 2010 may be increased. FIGS. 21A-21B are illustrations of a local area cosmogenic neutron sensor 2110 with a thermal neutron shield to improve signal-to-noise ratio and signal contrast, in accordance with the first exemplary embodiment of the present disclosure.

With reference to FIG. 21A first, as shown, the local area cosmogenic neutron sensor 2110 includes a standard hydrogen sensitive neutron detector 2120, which is also referred to as a standard cosmogenic-neutron soil moisture sensor (CNS) 2120, or just 'CNS 2120' for short. The local area CNS 2110 includes a generalized neutron shield 2130 which is positioned above the CNS 2120 and on the vertical sides of the CNS 2120, such that the shield 2130 covers or substantially covers all portions of the CNS 2120 except the face of the CNS 2120 which faces downwards, towards a measurement surface 2140. The neutron shield 2130 may, in a nonlimiting example, be a plastic material, such as HDPE or UHMW, of sufficient thickness, typically a minimum of 3", to absorb neutrons and prevent them from entering the CNS 2120. In the depiction of FIG. 21A, the measurement surface 2140 includes a land surface 2142 which comprises a quantity of soil 2144 having hydrogen atoms 2146 therein. In other examples, the measurement surface 2140 may include other settings for the measurement of neutrons, including water or liquid surfaces, vegetation, plants, substrates, or other locations.

Due to the shield 2130 not being positioned over the bottom face of the CNS 2120, the bottom face of the CNS 2120 is open to the measurement surface 2140 below it. Additionally, the CNS 2120 with the shield 2130 is supported in a position vertically above the measurement surface 2140 with a stand structure 2150, which may include any type of mechanical or electro-mechanical device or components which are capable of holding the CNS 2120 and shield 2130 above the measurement surface 2140. In FIG. 21A, the stand structure 2150 is depicted as simplistic columns which support the weight of the CNS 2120 and shield 2130, but it is noted the stand structure 2150 may include other supporting structures, such as scaffolding, cases, stands, land and/or air vehicles, human-carried structures such as backpacks, or any other structure. The CNS 2120 is held a distance 'D' (FIG. 21A) from the measurement surface 2140, where D can represent any distance, commonly one centimeter or greater, a few centimeters or greater, a meter or greater, or any other distance.

Due to the CNS 2120 and the shield 2130 located therearound in the position described herein, i.e., covering the top and vertical sidewalls of the CNS 2120 but not covering the bottom face of the CNS 2120, and the CNS 2120 being positioned a distance D above the measurement surface 2140, the CNS 2120 is preferentially sensitive to neutrons in the area of the measurement surface 2140 positioned immediately below the CNS 2120 and adjacent locations which are below and lateral to the CNS 2120. This area is collectively known as the 'local area', and as such, this configuration of the CNS 2120 with shield 2130 in the position described is a 'local area CNS' 2110.

While the exact location and dimensions of the local area may vary, depending on factors such as the size of the shield 2130, the value of distance D, and other factors, the local area is commonly understood as the area immediately below the physical footprint of the CNS 2120, e.g. the length and width spatial dimensions of the CNS 2120, as well as the surrounding areas of the measurement surface which are below the CNS 2120 and latterly offset from the physical footprint of the CNS 2120. In some cases, the local area may include an area of the measurement surface within a 5 meter radius of the CNS 2120, whereas in other cases, the local area may include a portion of the measurement surface within a 1 meter radius, a 2 meter radius, a 3 meter radius, a 4 meter radius, and/or a 10 meter radius, or greater, or any combination thereof.

The local area CNS 2110 further includes a thermal neutron shield 2160 which is placed on or below the bottom face of the CNS 2120, such that it is in a path of neutron travel between the measurement surface and the CNS 2120. The thermal neutron shield 2160 is different from shield 2130, in that, shield 2130 blocks neutrons with which it interacts, thereby preventing them reaching the CNS 2120 in the measurable energy range. These neutrons blocked by the shield 2130 include thermal neutrons (0.5 eV) 2102, epithermal neutrons (0.5 eV-1000 eV) 2104, and fast neutrons (1,000 eV or more) 2106. In contrast, the thermal neutron shield 2160 acts more like a filter by only blocking thermal neutrons 2102 below the range of approximately 1 eV, while allowing epithermal neutrons 2104 above approximately 1 eV to pass through. Thus, the thermal neutron shield 2160 acts to block low energy neutrons below the range ~1 eV without interacting with or otherwise affecting neutrons above ~1 eV. While different materials may be used as the thermal neutron shield 2160, an example of a thermal neutron shield 2160 is cadmium metal which blocks neutrons with energy below 0.5 eV. Other suitable materials may include boron or gadolinium, or another material which blocks thermal neutrons below some energy level or energy level range. The size, thickness, number of layers, or other parameters of the material or materials used for the thermal neutron shield 2160 may be varied, as dependent on the design of the local area CNS 2110.

As shown in FIG. 21A, the position of the thermal neutron shield 2160 is below the CNS 2120 along the bottom face thereof, such that the thermal neutron shield 2160 is substantially located across the opening of the shield 2130 and spans the distance of the exposed CNS 2120. Accordingly, in this position, the thermal neutron shield 2160 prevents thermal neutrons 2102 which arrive at the local area CNS 2110 from below from being measured in the CNS 2120, when the local area CNS 2110 is placed above the measurement surface 2140.

It is noted that the standard CNS 2120 includes a moderator 2122 that makes the neutron detector 2124 internal to the moderator 2122 sensitive to neutrons in a range of 1 eV to 1000 eV, or greater. Neutrons in this energy range are sensitive to environmental hydrogen and are considered as signal for the CNS 2120, whereas neutrons that have already been thermalized (<1 eV) by the environment, are considered signal noise if measured by the CNS 2120, in that, they degrade the quality of the signal reading of the CNS 2120. Thus, it is beneficial to filter out or block these neutrons which contribute to signal noise. Commonly, the CNS 2120 includes a thermal neutron detector 2124 surrounded by a moderator 2122 from 0.25" to 2" thick. In general, a subset of environmental thermal neutrons penetrates the moderator 2122 of the CNS 2120 and enters the thermal neutron detector 2124, and this contributes noise to the CNS 2120.

The amount of noise in the CNS 2120 may be dependent upon moderator 2122 thickness, however, it is impractical to increase the moderator 2122 thickness to prevent the noise due to the weight and bulk of the moderator 2122 material which would be required (such a CNS 2120 could be too heavy to move or transport in a practical way). Additionally, increasing the moderator 2122 thickness also has the disadvantage that it may decrease the amount of desired signal neutrons which are received at the CNS 2120, or it may outright block the desired signal neutrons from being received at the CNS 2120. Thus, the material of the moderator 2122, such as HDPE or a similar material, and the thickness of the moderator 2122 should be selected to ensure there is no decrease in signal quality of the desired neutrons, and also, secondarily, to minimize weight of the local area CNS 2110.

By use of the thermal neutron shield 2160 placed below the local area CNS 2110, the amount of environmental thermal neutrons 2102 that reach the CNS 2120 can be significantly reduced. Moreover, this reduction in the signal noise can be achieved with a very minimal increase in the bulk or weight of the local area CNS 2110. While increasing the thickness of the moderator 2122 will remove unwanted environmental neutrons, it will also have the negative effect of decreasing or blocking the desired neutrons from arriving at the CNS 2120. In contrast, the thermal neutron shield 2160 is able to remove the unwanted signal noise neutrons while not negatively affecting the desired signal neutrons. The thermal neutron shield 2160 is also light weight and thin, such that it does not add bulk or weight to the local area CNS 2110. Accordingly, by use of the thermal neutron shield 2160, it is possible to reduce this particular noise source in the detector 2124, thereby improving both its signal-to-noise ratio and signal contrast. In one example, the environmental thermal neutron background can be approximately 15% to 30% of the neutron counts in a detector with a moderator having a thickness of 0.25 inches to 2.0 inches, whereas using a thermal neutron shield 2160 can reduce the environmental thermal neutron background to substantially 0%.

It is further noted that while the thermal neutron shield 2160 reduces signal noise, it does not reduce the signal in the local area CNS 2110. This is because epithermal neutrons having energies above the cutoff energy of the thermal neutron shield 2160, e.g. approximately 1 eV, which arrive from below the CNS 2120 pass through the thermal neutron shield 2160 substantially unimpeded. Epithermal neutrons in the energy range 1 eV to 1000 eV, which represent signal in the CNS 2120, are above the cutoff energy of the thermal neutron shield 2160, such that they are not blocked.

With reference now to FIG. 21B, it depicts a local area cosmogenic neutron sensor 2112 which is similar to the local area CNS 2110 of FIG. 21A. Accordingly, the description of the components and features of the local area CNS 2110 of FIG. 21A applies to the local area CNS 2112 of FIG. 21B, except as otherwise noted. As shown in FIG. 21B, the local area CNS 2112 includes a detector 2124 which is a thermal neutron detector surrounded by a combination neutron moderator 2122 and shield 2130, and a thermal neutron shield 2160 is positioned on the bottom face of the detector 2124. In contrast to the local area CNS 2110 of FIG. 21A, however, the moderator 2122 of the local area CNS 2112 of FIG. 21B is not positioned along the bottom surface or face of the detector 2124.

The neutron moderator 2122, which surrounds the thermal neutron detector 2124 on the top and sides is a moderating material of sufficient thickness to moderate neutrons in the desired energy range for measurement, greater than 1 eV, such that they may be measured by the thermal neutron detector 2124. In one example, the thickness is typically 0.25 inches to 2.0 inches. The neutron shield 2130 surrounds the neutron moderator 2122 and detector 2124 on the top and sides. The neutron shield 2130 is a generalized neutron shield made from any material capable of blocking neutrons. The neutron shield 2130 prevents neutrons impingement upon the detector 2124 from above and from the sides from entering the thermal neutron detector 2124.

The neutron shield 2130 may, in one example, be a plastic material, such as HDPE or UHMW, of sufficient thickness, typically a minimum of 3", to absorb neutrons and prevent them from entering the thermal neutron detector 2124. In some cases, it is possible for both the moderator 2122 and the neutron shield 2130 to be made from the same material, where the combined thickness of the neutron moderator 2122 and neutron shield 2130 should be greater than 3.0 inches in all directions, preferably at least 6.0 inches. A local area CNS 2112 with this arrangement and configuration will be capable of substantially blocking neutrons arriving from above and from the sides.

As previously noted, the moderator 2122 is absent along the bottom face of the detector 2124. As such, fast neutrons, in the desired energy range for measurement, arriving from below the detector 2124 are not blocked from the detector 2124 and some subset of these neutrons pass through the detector 2124 largely undetected because it is not sensitive to neutrons with energy above the thermal range. However, upward traveling epithermal neutrons interact with the moderator 2122 and some subset of them are moderated down to the thermal energy range (1 eV or less) and backscattered into the thermal neutron detector 2124 where they can be measured. These epithermal and fast neutrons with energy >1 eV are sensitive to hydrogen and contribute signal to the thermal neutron detector 2124. If environmental thermal neutrons 2102 arrive at the thermal neutron detector 2124 from below, then they can be directly measured by the thermal neutron detector 2124 and they would contribute noise to the detector 2124. Thus, the removal of such upward traveling environmental thermal neutrons 2102 is desirable and improves the signal-to-noise ratio and signal contrast of the detector 2124.

Similar to that described relative to FIG. 21A, a thermal neutron shield 2160 is capable of blocking low energy (thermal) neutrons below 1 eV if placed at or below the bottom face of the detector 2124, such that it substantially spans the opening between the opposing sides of the moderator 2122 and/or the shield 2130. The thermal neutron shield 2160 prevents environmental thermal neutrons 2102 impingement upon the detector 2124 arriving from below from entering the thermal neutron detector 2124 and being measured. Environmental thermal neutrons 2102 are not within the desired energy range for measurement by the detector 2124 and are, therefore, a source of noise, as described relative to FIG. 21A. The thermal neutron shield 2160 can substantially reduce this noise by preventing these environmental thermal neutrons 2102 from being detected. As previously noted, the thermal neutron shield 2160 can be made from a material that blocks thermal neutrons below some energy level or energy level range. For example, suitable materials for the thermal neutron shield 2160 may include cadmium, boron and/or gadolinium, or another material which blocks thermal neutrons below some energy level or energy level range. The size, thickness, number of layers, or other parameters of the material or materials used for the thermal neutron shield 2160 may be varied, as dependent on the design of the local area CNS 2110.

In use, the local area CNS 2112 blocks fast neutrons impingement from above and from the sides which come from a wide area around the detector 2124. As the detector 2124 measures fast and epithermal neutrons in the desired energy range for measurement, arriving, substantially, from below in a local area, environmental thermal neutrons arriving from below are substantially blocked. As these neutrons are a source of noise, blocking them allows the local area CNS 2112 to have a higher spatial resolution than a conventional cosmic ray sensor because it is sensitive to local neutrons and blocks wide area signal neutrons that have sampled the measurement surface at a greater distance, outside the local area.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A local area cosmogenic neutron sensor for detecting moisture within a measurement surface, the local area cosmogenic neutron sensor comprising:
    a neutron detector positionable above the measurement surface, wherein a moderator material is positioned around at least a portion of the neutron detector to form a moderated neutron detector;
    a neutron shield positioned around a portion of the moderated neutron detector, whereby the neutron shield substantially covers lateral sides of the moderated neutron detector and substantially an entirety of a top of the moderated neutron detector, wherein the neutron shield is positioned to interact with cosmogenic neutrons propagating to the lateral sides or the top of the moderated neutron detector, thereby substantially blocking fast, epithermal, and thermal cosmogenic neutrons propagating to the lateral sides or the top of the moderated neutron detector from reaching the moderated neutron detector, and wherein the neutron shield is not positioned on a bottom side of the moderated neutron detector;
    a thermal neutron shield positioned below the neutron detector; and
    a stand structure holding the moderated neutron detector and the neutron shield in a position a spaced vertical distance above the measurement surface with the bottom side of the moderated neutron detector facing the measurement surface,
    wherein local area cosmogenic neutrons propagating from the measurement surface below and near the moderated neutron detector travel through an air space before arriving at the thermal neutron shield, wherein environmental thermal neutrons are blocked from arriving at bottom side of the moderated neutron detector.

2. The local area cosmogenic neutron sensor of claim 1, wherein the thermal neutron shield comprises cadmium.

3. The local area cosmogenic neutron sensor of claim 1, wherein the thermal neutron shield comprises boron.

4. The local area cosmogenic neutron sensor of claim 1, wherein the thermal neutron shield comprises gadolinium.

5. The local area cosmogenic neutron sensor of claim 1, wherein the thermal neutron shield is positioned extending between two or more sidewalls of the neutron shield in a position below the moderated neutron detector.

6. The local area cosmogenic neutron sensor of claim 1, wherein the thermal neutron shield is positioned extending between two or more sidewalls of the moderating material in a position below the moderated neutron detector.

7. The local area cosmogenic neutron sensor of claim 1, wherein the moderator material is positioned around an entirety of the neutron detector.

8. The local area cosmogenic neutron sensor of claim 1, wherein the moderator material is positioned around a top and lateral sides of the neutron detector but is not positioned on a bottom side of the neutron detector.

9. The local area cosmogenic neutron sensor of claim 1, wherein the thermal neutron shield reduces or prevents signal noise from environmental thermal neutrons.

10. A local area cosmogenic neutron sensor for detecting moisture within a measurement surface, and having an improved signal-to-noise ratio and signal contrast, comprising:
    a stand structure;
    a neutron detector positioned on the stand structure, the stand structure holding the neutron detector a spaced vertical distance above a measurement surface;
    a moderator material positioned around at least a portion of the neutron detector;
    a neutron shield positioned around a portion of the neutron detector and moderator material, whereby the neutron shield substantially covers lateral sides of the neutron detector and substantially an entirety of a top of the neutron detector, wherein the neutron shield is positioned to interact with cosmogenic neutrons propagating to the lateral sides or the top of the neutron detector, thereby substantially blocking cosmogenic neutrons propagating to the lateral sides or the top of the neutron detector from reaching the neutron detector, and wherein the neutron shield is not positioned on a bottom side of the neutron detector; and
    a thermal neutron shield positioned below the neutron detector and in a path of neutron travel between the measurement surface and the neutron detector, wherein the thermal neutron shield substantially blocks environmental thermal neutrons from reaching the neutron detector.

11. The local area cosmogenic neutron sensor of claim 10, wherein the thermal neutron shield comprises cadmium.

12. The local area cosmogenic neutron sensor of claim 10, wherein the thermal neutron shield comprises boron.

13. The local area cosmogenic neutron sensor of claim 10, wherein the thermal neutron shield comprises gadolinium.

14. The local area cosmogenic neutron sensor of claim 10, wherein the thermal neutron shield is positioned extending between two or more sidewalls of the neutron shield in a position below the neutron detector.

15. The local area cosmogenic neutron sensor of claim 10, wherein the thermal neutron shield is positioned extending between two or more sidewalls of the moderating material in a position below the neutron detector.

16. The local area cosmogenic neutron sensor of claim 10, wherein the moderator material is positioned around an entirety of the neutron detector.

17. The local area cosmogenic neutron sensor of claim 10, wherein the moderator material is positioned around a top and lateral sides of the neutron detector but is not positioned on a bottom side of the neutron detector.

18. The local area cosmogenic neutron sensor of claim 10, wherein the thermal neutron shield reduces or prevents signal noise from environmental thermal neutrons.

19. The local area cosmogenic neutron sensor of claim 10, wherein the moderating material and the neutron shield are formed from a same material.

20. A method for detecting local area cosmogenic neutrons for use in detecting moisture within a measurement surface, the method comprising the steps of:

positioning a neutron detector above the measurement surface, wherein a moderator material is positioned around at least a portion of the neutron detector to form a moderated neutron detector;

placing a neutron shield around a portion of the moderated neutron detector, whereby the neutron shield substantially covers lateral sides of the moderated neutron detector and substantially an entirety of a top of the moderated neutron detector, whereby the neutron shield is positioned to interact with cosmogenic neutrons propagating to the lateral sides or the top of the moderated neutron detector, thereby substantially blocking fast, epithermal, and thermal cosmogenic neutrons propagating to the lateral sides or the top of the moderated neutron detector from reaching the moderated neutron detector, and wherein the neutron shield is not positioned on a bottom side of the moderated neutron detector;

placing a thermal neutron shield in a position below the neutron detector; and spacing the moderated neutron detector a spaced vertical distance about the measurement surface with a stand structure, whereby the bottom side of the moderated neutron detector faces the measurement surface, whereby local area cosmogenic neutrons propagating from the measurement surface below and near the moderated neutron detector travel through an air space before arriving at the thermal neutron shield, whereby environmental thermal neutrons are blocked from arriving at bottom side of the moderated neutron detector.

* * * * *